US012740826B2

(12) United States Patent
Viswanathan et al.

(10) Patent No.: US 12,740,826 B2
(45) Date of Patent: Sep. 22, 2026

(54) SYSTEMS, APPARATUSES, AND METHODS FOR PRE-ABLATION PULSES IN PULSED FIELD ABLATION APPLICATIONS

(71) Applicant: Boston Scientific Scimed Inc., Maple Grove, MN (US)

(72) Inventors: Raju Viswanathan, Mountain View, CA (US); William Bowers, Westminster, CO (US); Colt Joseph Wilkins, Arvada, CO (US); Michael Alan Paré, San Carlos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 936 days.

(21) Appl. No.: 17/850,039

(22) Filed: Jun. 27, 2022

(65) Prior Publication Data

US 2023/0000547 A1 Jan. 5, 2023

Related U.S. Application Data

(63) Continuation of application No. 17/382,160, filed on Jul. 21, 2021, now Pat. No. 11,389,234.

(Continued)

(51) Int. Cl.

*A61B 18/18* (2006.01)
*A61B 18/12* (2006.01)

(Continued)

(52) U.S. Cl.

CPC ..................... *A61B 18/1492* (2013.01); *A61B 2018/00351* (2013.01); *A61B 2018/00577* (2013.01);

(Continued)

(58) Field of Classification Search

CPC ............ A61B 18/1206; A61B 18/1492; A61B 2018/00267; A61B 2018/00351;

(Continued)

(56) References Cited

U.S. PATENT DOCUMENTS 6,936,047 B2 * 8/2005 Nasab ................ A61B 18/1206 606/34
7,001,383 B2 2/2006 Keidar (Continued)

FOREIGN PATENT DOCUMENTS

CA 3135773 A1 12/2020
CN 112022331 A 12/2020

(Continued)

OTHER PUBLICATIONS

Notice of Reasons for Refusal received for Japanese Patent Application No. 2023-548683, mailed on Feb. 12, 2025, 23 pages (11 pages of English Translation and 12 pages of Original Document).

(Continued)

*Primary Examiner* — Michael F Peffley
*Assistant Examiner* — Amanda L Zink
(74) *Attorney, Agent, or Firm* — Nelson Mullins Riley & Scarborough LLP

(57) ABSTRACT

Systems, devices, and methods for electroporation ablation therapy are disclosed, with the system including a signal generator for generating pre-ablation signals and pulse waveforms for medical ablation therapy that may be coupled to an ablation device including at least one electrode for ablation pulse delivery to tissue. The signal generator may generate and delivery pre-ablation signals to subsets of electrodes of the ablation device and measure currents associated with the delivery to determine whether the currents meet one or more predetermined criteria. The signal generator may also generate and deliver voltage pulses to the ablation device in the form of a pulse waveform after determining that the currents meet the one or more predetermined criteria.

22 Claims, 17 Drawing Sheets

Related U.S. Application Data

(60) Provisional application No. 63/148,524, filed on Feb. 11, 2021.

(51) Int. Cl.
*A61B 18/14* (2006.01)
*A61B 18/00* (2006.01)

(52) U.S. Cl.
CPC ............... *A61B 2018/00613* (2013.01); *A61B 2018/00666* (2013.01); *A61B 2018/00767* (2013.01); *A61B 2018/00827* (2013.01); *A61B 2018/00898* (2013.01)

(58) Field of Classification Search
CPC ........... A61B 2018/00577; A61B 2018/00613; A61B 2018/00666; A61B 2018/00767; A61B 2018/00827; A61B 2018/00898
See application file for complete search history.

(56) References Cited

U.S. PATENT DOCUMENTS 7,842,031 B2 11/2010 Abboud et al.
7,892,232 B2 2/2011 Boese et al.
8,175,680 B2 5/2012 Panescu
8,357,152 B2 1/2013 Govari et al.
8,454,589 B2 6/2013 Deno et al.
8,478,379 B2 7/2013 Osadchy et al.
9,002,436 B2 4/2015 Wu et al.
9,123,099 B2 9/2015 Hundley et al.
9,173,611 B2 11/2015 Deno et al.
9,198,733 B2 12/2015 Neal et al.
9,204,927 B2 12/2015 Afonso et al.
9,265,557 B2 2/2016 Sherman et al.
9,283,026 B2 3/2016 Paul et al.
9,492,226 B2 11/2016 Fish et al.
9,757,182 B2 9/2017 Bustan et al.
9,980,652 B2 5/2018 Govari et al.
9,987,081 B1 * 6/2018 Bowers ............. A61B 18/1492
10,016,232 B1 7/2018 Bowers et al.
10,130,419 B2 11/2018 Deno et al.
10,201,388 B2 2/2019 Fish et al.
10,238,447 B2 3/2019 Neal et al.
10,349,824 B2 7/2019 Claude et al.
10,675,086 B2 6/2020 Afonso et al.
10,702,326 B2 7/2020 Neal et al.
10,792,087 B2 10/2020 Altmann et al.
10,792,097 B2 10/2020 Ziv-Ari et al.
10,842,572 B1 11/2020 Viswanathan
10,856,771 B2 12/2020 Bar-Tal et al.
10,881,455 B2 1/2021 Schwartz et al.
10,888,373 B2 1/2021 Koblish et al.
10,893,903 B2 1/2021 Koblish et al.
11,039,888 B2 6/2021 Schwartz et al.
11,116,585 B2 9/2021 Lyons et al.
11,135,008 B2 10/2021 Govari et al.
11,324,550 B2 5/2022 Deno et al.
11,369,428 B2 6/2022 Laughner et al.
11,389,234 B1 7/2022 Viswanathan et al.
11,596,471 B2 3/2023 Schroeder
11,617,618 B2 4/2023 Koblish et al.
11,622,713 B2 4/2023 Ben-Haim et al.
11,737,817 B2 8/2023 Lyons et al.
11,744,515 B2 9/2023 Rodriguez et al.
11,793,576 B2 10/2023 Schwartz et al.
11,890,046 B2 2/2024 Neal et al.
12,023,091 B2 7/2024 Schwartz et al.
12,076,131 B2 9/2024 Osadchy et al.
12,161,422 B2 12/2024 Wright et al.
12,201,352 B2 1/2025 Deno et al.
2008/0071263 A1 3/2008 Blaha
2008/0275440 A1 11/2008 Kratoska et al.
2009/0177111 A1 7/2009 Miller et al.
2014/0276766 A1 9/2014 Brotz et al.
2016/0242667 A1 8/2016 Fay et al.
2020/0155227 A1 * 5/2020 Cao ................... A61B 18/1482
2020/0155228 A1 5/2020 Salehi et al.
2020/0230403 A1 7/2020 Bowers et al.
2020/0297415 A1 9/2020 Marshik et al.
2020/0345304 A1 11/2020 Joshi et al.
2021/0169394 A1 6/2021 Chou et al.
2021/0369341 A1 12/2021 Gutbrod et al.
2022/0005198 A1 1/2022 Goldberg et al.
2022/0036560 A1 2/2022 Amos et al.
2022/0226046 A1 7/2022 Mariappan et al.
2022/0401146 A1 12/2022 Asconeguy et al.
2023/0077196 A1 3/2023 Curran
2024/0225724 A9 7/2024 Govari
2025/0387160 A1 12/2025 Laughner et al.

FOREIGN PATENT DOCUMENTS

JP 2020-518335 A 6/2020
JP 2021-500153 A 1/2021
WO 2021/078918 A1 4/2021
WO 2022/173875 A1 8/2022

OTHER PUBLICATIONS

Notice of Reasons for Refusal received for Japanese Patent Application No. 2023-548683, mailed on Jun. 11, 2024, 16 pages (8 pages of English Translation and 8 pages of Original Document).
International Search Report and Written Opinion received for PCT Patent Application No. PCT/US2022/015881, mailed on May 12, 2022, 14 pages.
Intention to grant received for European Patent Application No. 25170231.2, mailed on Feb. 24, 2026, 6 pages.
Extended European Search Report and Search Opinion received for European Application No. 25170231.2, mailed on May 28, 2025, 5 pages.
Office Action received for Chinese Patent Application No. 202280014663.1, mailed on Apr. 16, 2026, 18 pages (9 pages of English Translation and 9 pages of Original Document).

* cited by examiner

Current Measurement for Short Pre-Ablation Pulses

Current Measurement for Ultra-short Pre-Ablation Pulses

SYSTEMS, APPARATUSES, AND METHODS FOR PRE-ABLATION PULSES IN PULSED FIELD ABLATION APPLICATIONS

CROSS-REFERENCE TO RELATED APPLICATIONS

This application is a Continuation application that claims priority to U.S. application Ser. No. 17/382,160, filed Jul. 21, 2021, now issued as U.S. Pat. No. 11,389,234, which claims priority to U.S. Provisional Patent Application No. 63/148,524, filed on Feb. 11, 2021, the entire disclosure of which is incorporated herein by reference in its entirety.

BACKGROUND

Pulsed electric field energy delivery, also known as Pulsed Field Ablation (PFA), utilizes brief pulses of high voltage that generate locally high electric fields that can drive the breakdown of cell membranes and result in cell death, a process also referred to as irreversible electroporation. In a fluid medium (for example, such as blood), high voltage pulses may result in electrolysis and associated bubble generation. In some cases, depending on pulse amplitude and waveform, the electric field very close to an electrode edge can be high enough to drive localized thermal effects or result in local flash arcing events, which can be undesirable for clinical applications such as cardiac ablation. Accordingly, it can be desirable to ensure that a device is appropriately positioned and deployed relative to target tissue prior to ablation energy delivery.

SUMMARY

Described herein are systems, devices, and methods for ablating tissue through irreversible electroporation. In some embodiments, a system can include an ablation device including a set of electrodes configured to be positioned within patient anatomy; a signal generator including: an energy source coupled to the set of electrodes, and sensing circuitry coupled to the set of electrodes; and a processor operatively coupled to the energy source and the sensing circuitry, the processor configured to: generate, using the energy source, a set of pre-ablation signals; deliver the set of pre-ablation signals to a first set of subsets of electrodes of the set of electrodes; measure, using the sensing circuitry, a set of one or more currents passing through a current sense resistor of the sensing circuitry in response to the delivery of the set of pre-ablation signals; determine whether the set of currents meet a predetermined criterion; and in response to determining that the set of currents meet the predetermined criterion, generate and deliver a pulse waveform to a second set of subsets of electrodes of the set of electrodes such that the second set of subsets of electrodes generates a pulsed electric field for ablating tissue.

In some embodiments, a signal generator or a separate measurement device can include an analog optocoupler coupled to the sensing circuitry, the analog optocoupler configured to isolate high-voltage noise from the signals measured by the sensing circuitry; and an analog-to-digital converter (ADC) configured to digitize the signals after the analog optocoupler has isolated the high-voltage noise from the signals and to pass the signals to the processor, and the processor can be configured to determine whether the set of currents meets the predetermined criterion after receiving the signals from the ADC.

In some embodiments, a signal generator or a separate measurement device can include a current sense resistor coupled to a set of electrodes of an ablation device positionable within patient anatomy; current measurement circuitry configured to measure a current across the current sense resistor that is generated in response to a pre-ablation pulse being applied to a first subset of electrodes of the set of electrodes; a comparator configured to determine whether the current meets a predetermined criterion and to produce a digital output indicative of whether the current meets the predetermined criterion; and a processor configured to: in response to the digital output indicating that the current meets the predetermined criterion, cause delivery of a pulse waveform to a second subset of electrodes of the set of electrodes such that the second subset of electrodes generates a pulsed electric field for ablation; and in response to the digital output indicating that the current does not meet the predetermined criterion, inhibit delivery of the pulse waveform to the second subset of electrodes.

In some embodiments, generating, using an energy source, a set of pre-ablation signals; delivering the set of pre-ablation signals to a first set of subsets of electrodes of the set of electrodes of an ablation device, the ablation device being position within patient anatomy; measuring, using sensing circuitry coupled to the set of electrodes, a set of one or more currents passing through a current sense resistor of the sensing circuitry in response to the delivery of the set of pre-ablation signals; determining whether the set of currents meet a predetermined criterion; and in response to determining that the set of currents meet the predetermined criterion, generating and delivering a pulse waveform to a second set of subsets of electrodes of the set of electrodes such that the second set of subsets of electrodes generates a pulsed electric field for ablating tissue.

BRIEF DESCRIPTION OF THE DRAWINGS

FIG. 4B is a schematic illustration of a front view of a deployed basket configuration of a deployable multi-spline catheter where the distal portion of the catheter comprises multiple splines that can be deployed over a range of configurations and where the splines are in a non-uniform arrangement due to anatomical constraints, according to embodiments.

DETAILED DESCRIPTION

Systems, devices, and methods described herein can be configured to determine the sufficiency of electrode positioning of an ablation device relative to tissue and to control the operation of an ablation device based on such determination. For example, a system as described herein may include a signal generator configured to generate pre-ablation pulses and measurement circuitry configured to measure the current of the pre-ablation pulses. The measured currents may be analyzed to determine an electrode distribution relative to tissue. In some embodiments, it can be beneficial to ensure that the that the current delivered for a given electrode pairing with a high voltage applied across the electrode pair is within a desirable range, or that the current is not excessively large, or that the currents satisfy other constraints for an optimal therapeutic effect. This can help assess device deployment for optimal ablation delivery. Systems, devices, and methods described herein deliver and measure pre-ablation currents before an ablation waveform is delivered in order to ensure appropriate device deployment prior to ablation delivery.

A status signal may be output and used to control delivery of ablation energy to tissue. For example, ablation energy delivery can be inhibited when an electrode distribution does not meet predetermined criteria. A user alert can be output to prompt device redeployment/repositioning prior to ablation energy delivery. Pre-ablation pulses as described herein can be generated and associated current measurements can be performed with a variety of interventional or minimally-invasive devices such as catheters for cardiac ablation.

Figure 13A:
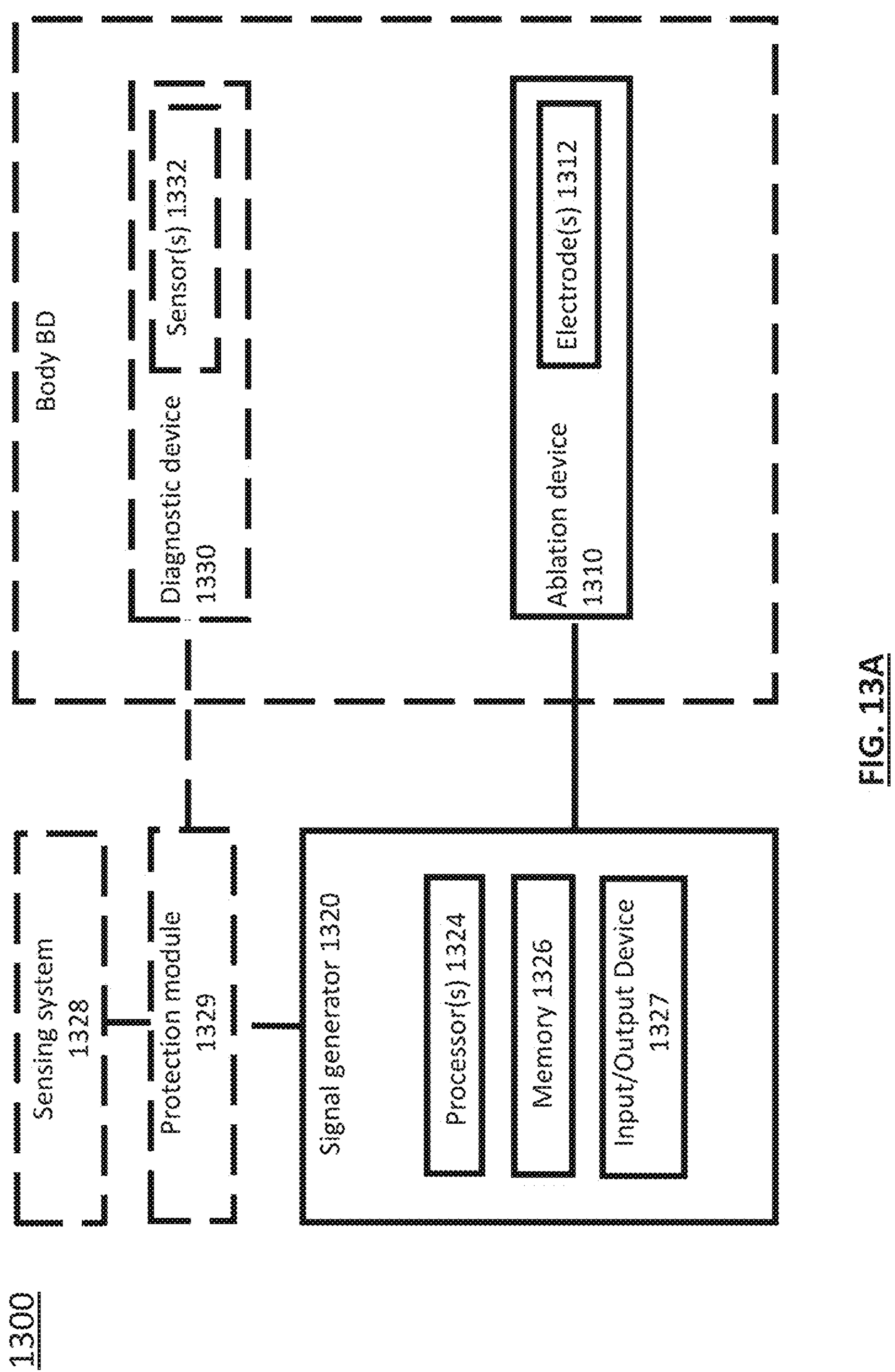
FIGS. 13A and 13B are block diagrams of a system for ablation, according to embodiments.

Generally, the systems and devices described herein include one or more devices (e.g., catheters) configured to ablate tissue in a heart (e.g., a left atrial chamber of a heart). FIG. 13A illustrates a system 1300 configured to deliver pre-ablation signals and ablation signals, according to embodiments. The system 1300 may include an ablation device 1310, and signal generator 1320, and optionally a sensing system 1328, protection device or module 1329, and diagnostic device 1330. The ablation device 1310 may include one or more electrodes 1312, and the diagnostic device 1330 may include one or more sensors 1332. The ablation device 1310 and diagnostic device 1330 can be disposable within a body BD of a patient. The ablation device 1310 may be coupled to a signal generator 1320 comprising processor(s) 1324, memory 1326, and input/output device 1327. In some embodiments, the signal generator 1320 can include a capacitor bank that stores energy for generating a pulse waveform that can be delivered to the ablation device 1310. In some embodiments, the generation and delivery of the pulse waveform can be controlled by one or more processor(s) 1324. Suitable examples of signal generators are described in U.S. Pat. No. 9,987,081, filed Apr. 27, 2017, titled "SYSTEMS, DEVICES, AND METHODS FOR SIGNAL GENERATION," now issued as U.S. Pat. No. 9,987,081, the disclosure of which is incorporated herein by reference.

Each of the one or more processor(s) 1324 may be any suitable processing device configured to run and/or execute a set of instructions or code. The processor(s) 1324 may be, for example, a general purpose processor, a Field Programmable Gate Array (FPGA), an Application Specific Integrated Circuit (ASIC), a Digital Signal Processor (DSP), a microcontroller, a microprocessor, and/or the like (e.g., a combination comprising multiple processors and/or multiple types of processors. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like. In some embodiments, the processor(s) 1324 can be configured to control generation and/or delivery of pre-ablation pulses and/or an ablation waveform to the ablation device 1310.

The memory 1326 may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory 1326 may store instructions to cause the processor 1324 to execute modules, processes and/or functions, such as, for example, pre-ablation pulse and/or pulse waveform generation.

The input/output device 1327 can include one or more components configured for receiving an input and/or generating an output to a user. For example, the input/output device 1327 can include a user interface, such as a display, audio device, touchscreen device, etc. The input/output device 1327 can include one or more interfaces for communicating with external devices, e.g., the ablation device 1310, the diagnostic device 1330, the protection module 1329, and/or the sensing system 1328.

The ablation device 1310 can be any suitable device configured to deliver ablation energy to tissue. In some embodiments, the ablation device 1310 can include a catheter with sets of electrode(s) 1312 that are configured to generate a pulsed electric field for ablating tissue via irreversible electroporation. In some embodiments, the ablation device 1310 can be movable or transitionable between a plurality of configurations. In some embodiments, the ablation device 1310 can have a basket structure, a linear structure, a flower structure, a lasso structure, a balloon structure, and/or any other suitable structure for delivering ablation energy to tissue. Suitable examples of ablation devices are described in International Application No. PCT/US2018/029938, filed on Apr. 27, 2018, titled "SYSTEMS, DEVICES, AND METHODS FOR DELIVERY OF PULSED ELECTRIC FIELD ABLATIVE ENERGY TO ENDOCARDIAL TISSUE," International Application No. PCT/US2020/026682, filed Apr. 3, 2020, titled "SYSTEMS, DEVICES, AND METHODS FOR FOCAL ABLATION," International Application No. PCT/US2020/037948, filed on Jun. 16, 2020, titled "SYSTEMS, DEVICES, AND METHODS FOR FOCAL ABLATION," and International Application No. PCT/US2018/050660, filed Sep. 12, 2018, titled "SYSTEMS, APPARATUSES, AND METHODS FOR VENTRICULAR FOCAL ABLATION," the contents of each of which are hereby incorporated by reference in their entirety.

The protection module 1329 can be coupled to a sensing system 1328, a diagnostic device 1330 and the signal generator 1320. The signal generator 1320 can be coupled to the ablation device 1310 and be configured to generate and deliver a high voltage signal to the electrode(s) 1312. The electrode(s) 1312 can be disposed near cardiac tissue of a heart of a subject. The diagnostic device 1330 including sensor(s) 1332 may be disposed near the electrode(s) 1312, e.g., in a cardiac chamber, or it may be disposed on or near an external surface of the subject. In some embodiments, delivery of the high voltage signal (e.g., a pulsed ablation waveform) to the electrode(s) 1312 of the ablation device 1310 may induce high currents and/or voltages within the sensor(s) 1332. These large unbalanced currents and/or voltages can disrupt the operation of the sensing system 1328. Accordingly, the protection module 1329 can be configured to decouple the sensing system 1328 from the diagnostic device 1330 during intervals of time associated with delivery of a high voltage signal to the ablation device 1310 such that the sensing system 1328 can be protected from high currents and/or voltages induced at the diagnostic device 1330. Suitable examples of protection modules and devices are described in International Patent Application No. PCT/US20/061564, filed Nov. 20, 2020, titled "SYSTEMS, APPARATUSES, AND METHODS FOR PROTECTING ELECTRONIC COMPONENTS FROM HIGH POWER NOISE INDUCED BY HIGH VOLTAGE PULSES," the disclosure of which is incorporated herein by reference.

In some embodiments, the sensing system 1328, when coupled to the diagnostic device 1330, may be configured to receive a measured signal from the sensor(s) 1332 of the diagnostic device 1330. In some embodiments, the diagnostic device 1330 can be an electrophysiology (EP) catheter configured to measure electrical signals from the body of a subject. In some embodiments, the measured signal can include an electrocardiogram (ECG) signal. In some embodiments, the sensing system 1328 can be configured to detect whether there is ectopic activity and/or pacing capture, and send one or more signals to the signal generator 1320 to control delivery of one or more pulse waveforms. For example, in response to detecting ectopic activity, the sensing system 1328 can be configured to send a signal to the signal generator 1320 that informs the signal generator 1320 of the ectopic activity and/or instructs the signal generator 1320 to pause or terminate signal waveform generation. Alternatively or additionally, in response to confirming pacing capture, the sensing system 1328 can be configured to send a signal to the signal generator 1320 that indicates to the signal generator 1320 that pacing capture has been confirmed and/or instructs the signal generator 1320 to initiate signal waveform generation. In some embodiments, one or more of the sensing functions such as detection of ectopic activity or confirmation of pacing capture can be performed by the signal generator 1320 based on signals received from the protection module 1329. Suitable examples of a controller or device for sensing information about a subject are described in U.S. patent application Ser. No. 16/573,704, filed Sep. 17, 2019, titled "SYSTEMS, APPARATUSES, AND METHODS FOR DETECTING ECTOPIC ELECTROCARDIOGRAM SIGNALS DURING PULSED ELECTRIC FIELD ABLATION," now issued as U.S. Pat. No. 10,625,080, the disclosure of which is incorporated herein by reference.

In some embodiments, the signal generator 1320 may be configured to generate pre-ablation pulse waveforms and/or ablation pulse waveforms. For example, the signal generator 1320 may be a voltage pulse waveform generator that generates and delivers a pre-ablation signal waveform and/or an ablation pulse waveform to the ablation device 1310. In some embodiments, the processor(s) 1324 may execute instructions stored in memory 1326 and/or incorporate data stored in memory 1326 and/or received from input/output device 1327 to control the signal generator 1320 to generate a pre-ablation signal or a pulse waveform having certain predefined parameters (e.g., timing, amplitude, pulse width, delay, etc.). The memory 1326 may store instructions that cause the signal generator 1320 to execute modules, processes and/or functions, such as pre-ablation deployment verification and pulse waveform generation. For example, the memory 1326 may be configured to store one or more of pre-ablation data and pulse waveform data. In some embodiments, the pre-ablation pulses and/or ablation pulses can have an amplitude of 100 V, 200 V, 300 V, 400 V, 500 V, 1 kV, 5 kV, 10 kV, or 20 kV, including all values and ranges in-between. In some embodiments, the pre-ablation pulse(s) can have smaller amplitude than the ablation pulse waveform. In some embodiments, the pre-ablation pulse(s) can have the same amplitude as the ablation pulse waveform. In some embodiments, the pre-ablation pulse(s) can have smaller pulse widths than pulses of the ablation pulse waveform. In some embodiments, the pre-ablation pulse(s) can have the same pulse width as the pulses of the ablation pulse waveform.

In some embodiments, the processor(s) 1324 can be configured to analyze signals measured at a current sense resistor (not depicted), and to control pulse ablation delivery based on the measured signals. For example, a sensing circuit including a current sense resistor can be coupled to the path of currents passing through electrode(s) 1312 of the ablation device 1310, and current passing through the sensing circuit can be processed and/or analyzed by the processor(s) 1324. In some embodiments, the processor(s) 1324 can control the signal generator 1320 to generate and deliver pre-ablation pulses to the electrode(s) 1312 of the ablation device 1310, and the signals passing through the sensing circuit can be processed and/or analyzed to determine whether they conform to one or more predetermined measures or criteria. For example, the sensed signals can be analyzed to check that each lies within a predetermined range of minimum and maximum values. In embodiments, the check can comprise determining that no signal exceeds a predetermined threshold value (e.g., a maximum value). In some embodiments, the check can comprise determining that no signal is below a predetermined threshold value (e.g., a minimum value). In embodiments, the check can comprise computing a metric such as the average value of the sensed signals. In embodiments the check can comprise computing a metric such as the variance of the sensed signals, computing a metric such as the ratio of maximum to minimum sensed signals, or computing a metric based on some other generally non-linear function of the sensed signals. In embodiments, the check can comprise any combination of these computations (e.g., a metric based on one or more of the computations described herein), and then determining whether the computed metric(s) lie inside a predetermined range or whether they fall below or exceed (e.g., are greater than or less than) appropriate predetermined threshold values. For example, in one embodiment the check can be to determine whether the variance of the measured currents lies within a certain range. As another example, in one embodiment, the check can be to determine whether the ratio of the maximum current to minimum current lies below a threshold value. In some embodiments, this threshold value can be greater than about 1 and less than about 5, greater than about 1 and less than about 10, greater than about 1 and less than about 20, including all sub-values and ranges in-between. In one embodiment, the predetermined range or threshold values can be user-adjustable, e.g., via inputs received from input/output device 1327. In some embodiments, the checks and/or predetermined ranges and values can vary depending on a type of ablation device being used, e.g., a linear ablation device vs. a basket device vs. a lasso device.

Figure 13B:
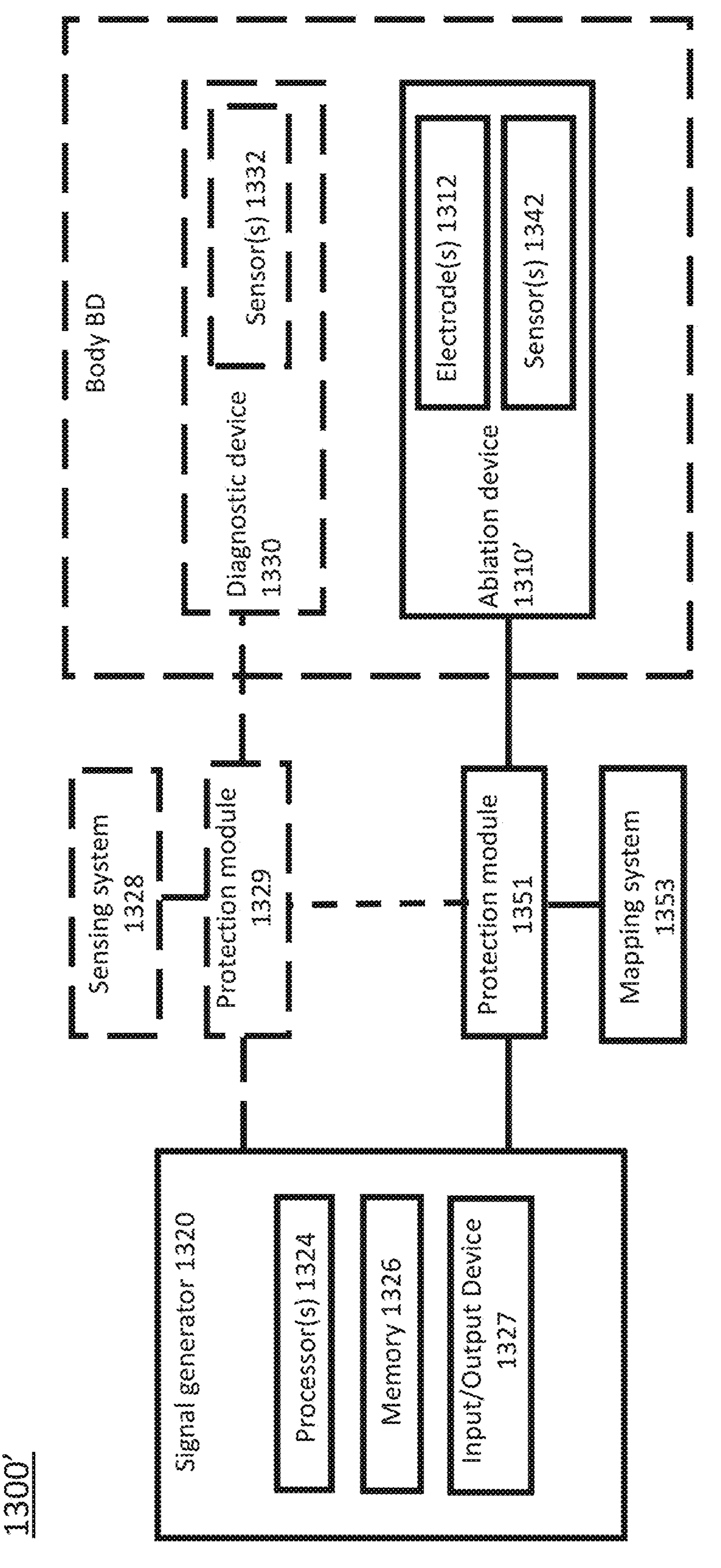

FIG. 13B illustrates a system 1300' configured to deliver pre-ablation signals and ablation waveforms, according to embodiments. The system 1300' can include components that are structurally and/or functionally similar to other ablation systems described herein, including ablation system 1300. For example, the system 1300' may include an ablation device 1310', signal generator 1320, a protection module 1329, a sensing system 1328, and a diagnostic device 1330. In addition, the system 1300' can include a protection module 1351 that is coupled to a mapping system 1353, the signal generator 1320 and the ablation device 1310'. The ablation device 1310' can be structurally and/or functionally similar to the ablation device 1310, but the ablation device 1310' can additionally include sensor(s) 1342 (e.g., electrodes, sensors) that can be configured to sense signals, e.g., in response to an electric of magnetic field for determining a position, location, and/or orientation of the ablation device 1310'. The ablation device 1310' and diagnostic device 1330 may be disposed within a body BD of a patient. The ablation device 1310' may be coupled to the signal generator 1320, which can include processor(s) 1324, memory 1326, and input/output device 1327.

In use, a signal waveform generated by signal generator 1320 may be delivered to the ablation device 1310', e.g., in some embodiments through second protection module 1351. Signals received from one or more of the sensors 1342 of the ablation device 1310' may be received by mapping system 1353, e.g., via protection module 1351. In some embodiments, protection module 1351 may be a modular extension of protection module 1329 (indicated in FIG. 13B by a dotted line from protection module 1329 to protection module 1351). For example, a single protection module can include multiple channels that are configured to isolate different electronic devices, e.g., sensing system 1329 and/or mapping system 1353, from high voltages and currents induced in devices upon ablation delivery. Accordingly, the protection modules 1329, 1351 can be part of a signal protection device. In some embodiments, multiple protection devices can be used, including separate protection modules 1329 and 1351. In some embodiments, one or more protection modules can form accessory devices attached to the signal generator.

The mapping system 1353 can be used with the sensor(s) 1342 to determine a position, location, and/or orientation of the ablation device 1310'. For example, the mapping system 1353 can include a field generator for generating an electric and/or magnetic field. The electric and/or magnetic field can cause the sensor(s) 1342 to receive signals that can be passed back to a processor (e.g., processor 1324 or a processor (not depicted) of the mapping system 1353). The processor can then process the signals to determine the position, location, and/or orientation of the ablation device 1310'. Suitable examples of mapping systems and how they can be used with ablation devices described herein are described in U.S. patent application Ser. No. 16/785,392, filed Feb. 7, 2020, and International Patent Application No. PCT/US20/61809, filed Nov. 23, 2020, both titled "METHODS, SYSTEMS, AND APPARATUSES FOR TRACKING ABLATION DEVICES AND GENERATING LESION LINES," the disclosures of each of which are incorporated herein by reference.

The system 1300, 1300' may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

Generally, the spatial arrangement of electrodes of an apparatus (e.g., catheter such as, for example, ablation device 1310, 1310') can have a significant role in PFA energy therapy delivery. An optimal range of distribution or placement of the electrodes (e.g., electrode(s) 1312) can ensure that therapy is delivered safely and effectively. For example, one or more of the local anatomy, geometry, and device placement may result in a sub-optimal distribution of the device electrodes. The systems, devices, and methods described herein may identify a sub-optimal distribution of electrodes, and can alert the user to reposition or redeploy the ablation device to optimize ablation device deployment or placement.

In some embodiments, pre-ablation pulses may be generated and delivered to tissue via medical device electrodes (e.g., electrode(s) 1312), and associated currents may be measured to enable a determination of whether to proceed with ablation energy delivery. In some embodiments, ablation energy delivery may proceed if the measured currents are within a predetermined range (e.g., currents are not excessively large) or satisfy predetermined constraints or criteria. In some embodiments, the ablation delivery may proceed immediately (e.g., with a small time delay) after satisfying the predetermined constraints based on the measured currents. If one or more of the constraints is not satisfied, ablation energy delivery does not occur and a message may be output to the user (e.g., visual display, audible tone). In some embodiments, a user interface display of an ablation system (e.g., input/output device 1327) can prompt the user to reposition and/or redeploy the ablation device (e.g., ablation device 1310, 1310'). After repositioning the ablation device, another set of pre-ablation pulses may be generated, e.g., to evaluate whether further repositioning is required before delivery of PFA.

Figure 1A:
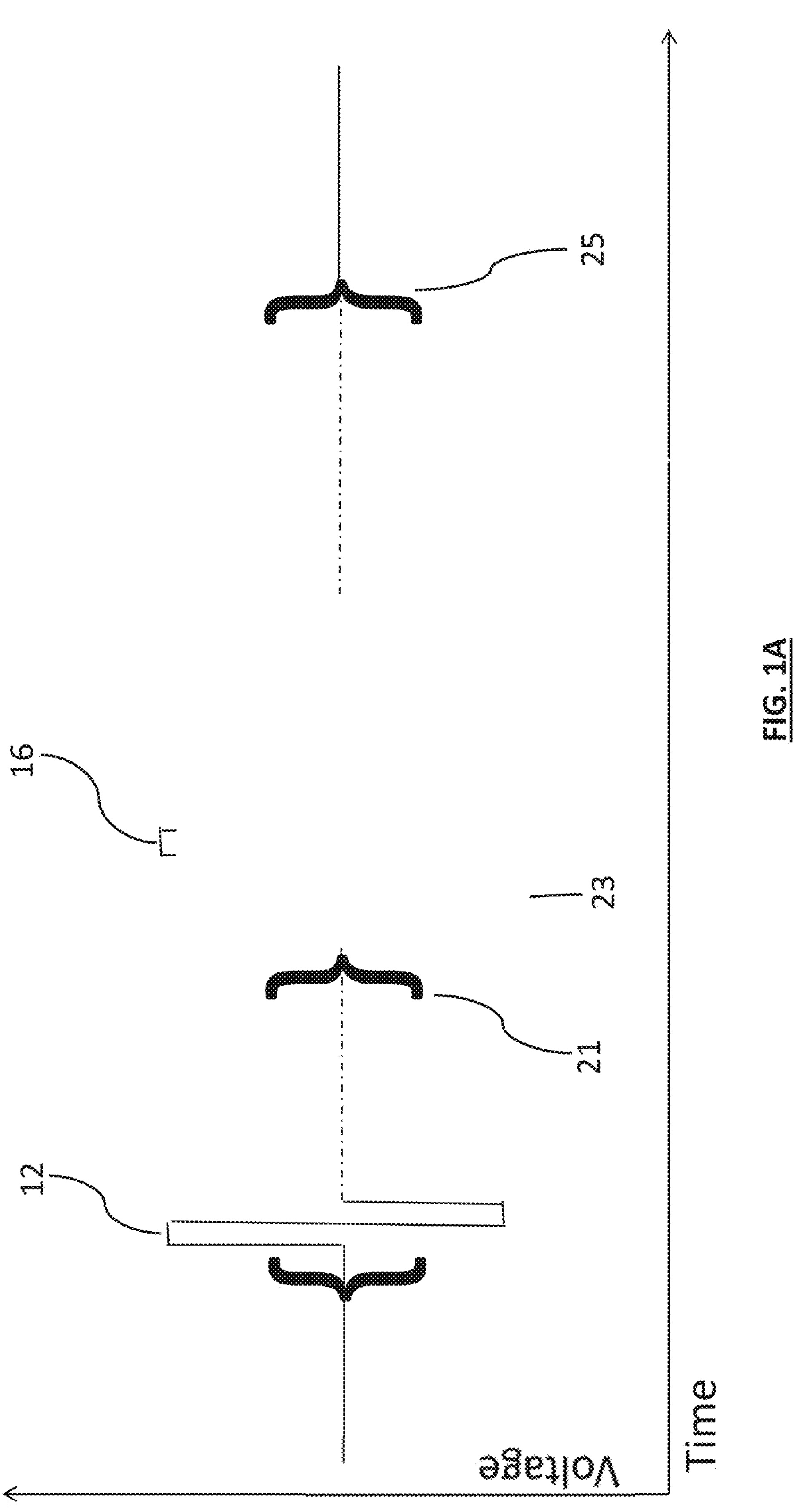
FIG. 1A schematically illustrates a set of voltage pre-ablation pulses, followed by a set of ablation pulses or ablation waveform, according to embodiments.

FIG. 1A schematically illustrates an example of pre-ablation signals followed by ablation signals, according to embodiments. The pre-ablation signals can include a set 21 of voltage pre-ablation pulses 12 followed by a set 25 of ablation pulses 16 (also referred to as the ablation waveform), with the pulses being delivered to a medical device (e.g., an ablation device 1310, 1310') engaging tissue in a subject anatomy and connected to a pulsed field ablation generator (e.g., signal generator 1320). Pre-ablation current measurements of the pre-ablation pulse set 21 may determine whether the set 25 of ablation pulses 16 is delivered after a time delay 23. In some embodiments, the time delay 23 between the end of the set of pre-ablation pulses 21 and a start of the set 25 of ablation pulses 16 can be in the range of about microseconds to about milliseconds, or about milliseconds to about seconds, including all ranges and sub-values in-between. While FIG. 1A illustrates biphasic pre-ablation pulses 12 and biphasic ablation pulses 16, it can be appreciated that in other embodiments, one or more of pre-ablation pulses may comprise monophasic pulses.

Figure 1B:
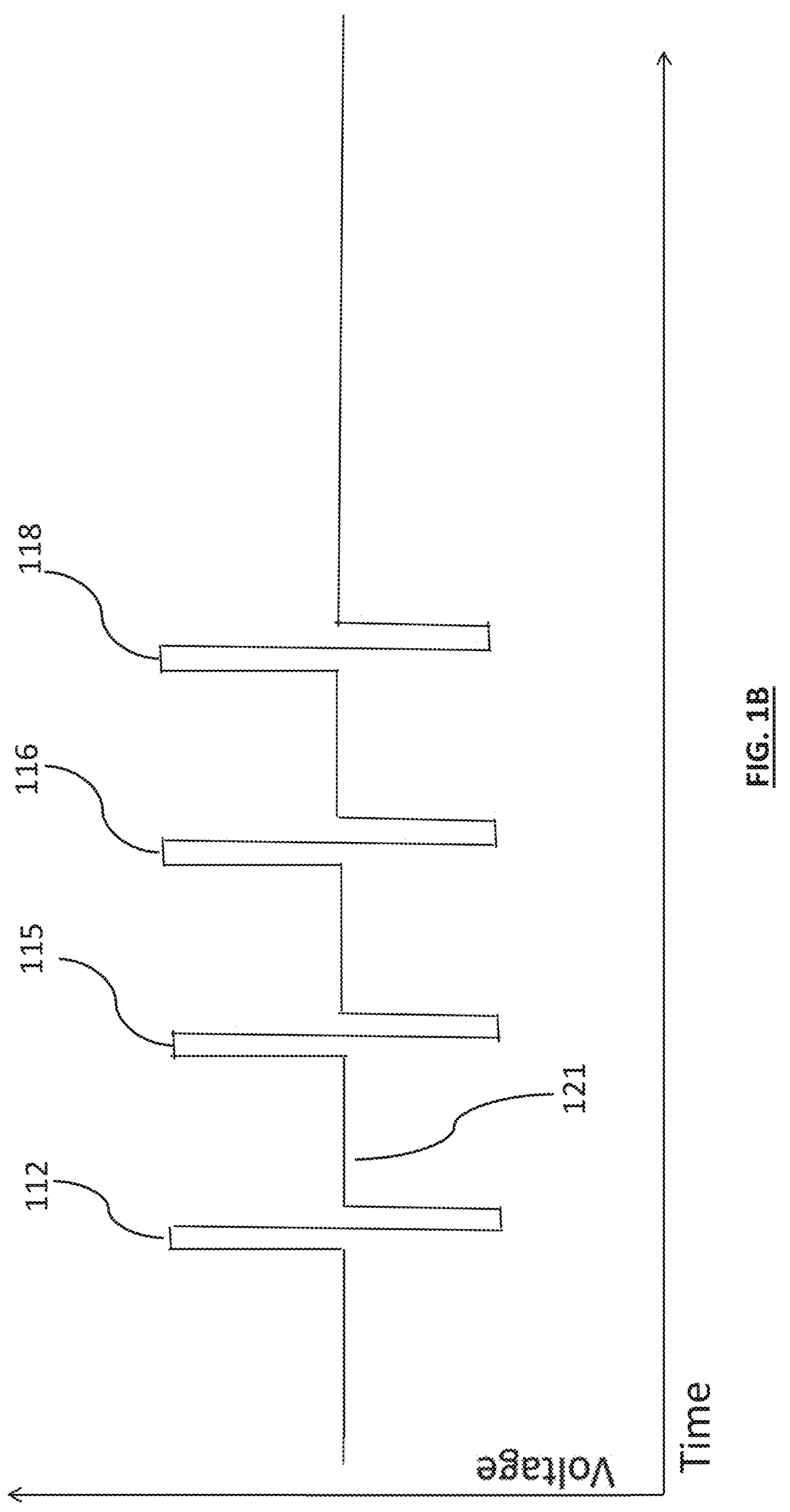
FIG. 1B schematically illustrates a set of voltage pre-ablation pulses, each applied to a distinct paired set of electrodes, according to embodiments.

FIG. 1B is a schematic illustration of a set of voltage pre-ablation pulses, each applied to a distinct pair or grouping of electrode subsets of an ablation device (e.g., ablation device 1310, 1310'). For example, each of pulses 112, 115, 116, and 118 are biphasic voltage pulses applied to a distinct pair of electrode subsets, with the respective subsets in each pair at opposite electrical polarities. Successive pulses such as 112 and 115 applied to different paired electrode subsets may be separated by a time delay 121. The time delay 121 can lie in the range of between about a microsecond to about a millisecond, or about tens of nanoseconds to about seconds, including all values and sub-ranges in between. In some embodiments, each pair of electrode subsets receiving an individual pre-ablation pulse is an electrode subset pair that can also receive a pulse waveform during ablation delivery. Alternatively, different electrode subsets can receive the pre-ablation pulses and the ablation pulse waveform. For example, a first set of subsets of electrodes can receive the pre-ablation pulses, and a second set of subsets of electrodes can receive an ablation pulse waveform for delivery of ablation therapy. The current delivered during each pre-ablation pulse may be measured as described in more detail with respect to later figures presented herein.

While FIG. 1B depicts four distinct pulses 112, 115, 116, and 118, it should be apparent to one skilled in the art that any number of pulses can be utilized and correspond to the number of distinct pairs of electrode subsets needed for the measurement. For example and in some embodiments, the number of pulses can correspond to the number of electrode subsets receiving ablation energy. Alternatively, the number of pulses can be greater than or less than the number of electrode subsets receiving ablation energy. Likewise, while FIG. 1B illustrates biphasic pre-ablation pulses 112, 115, 116, and 118, the pre-ablation pulses may comprise monophasic pulses.

Figure 2:
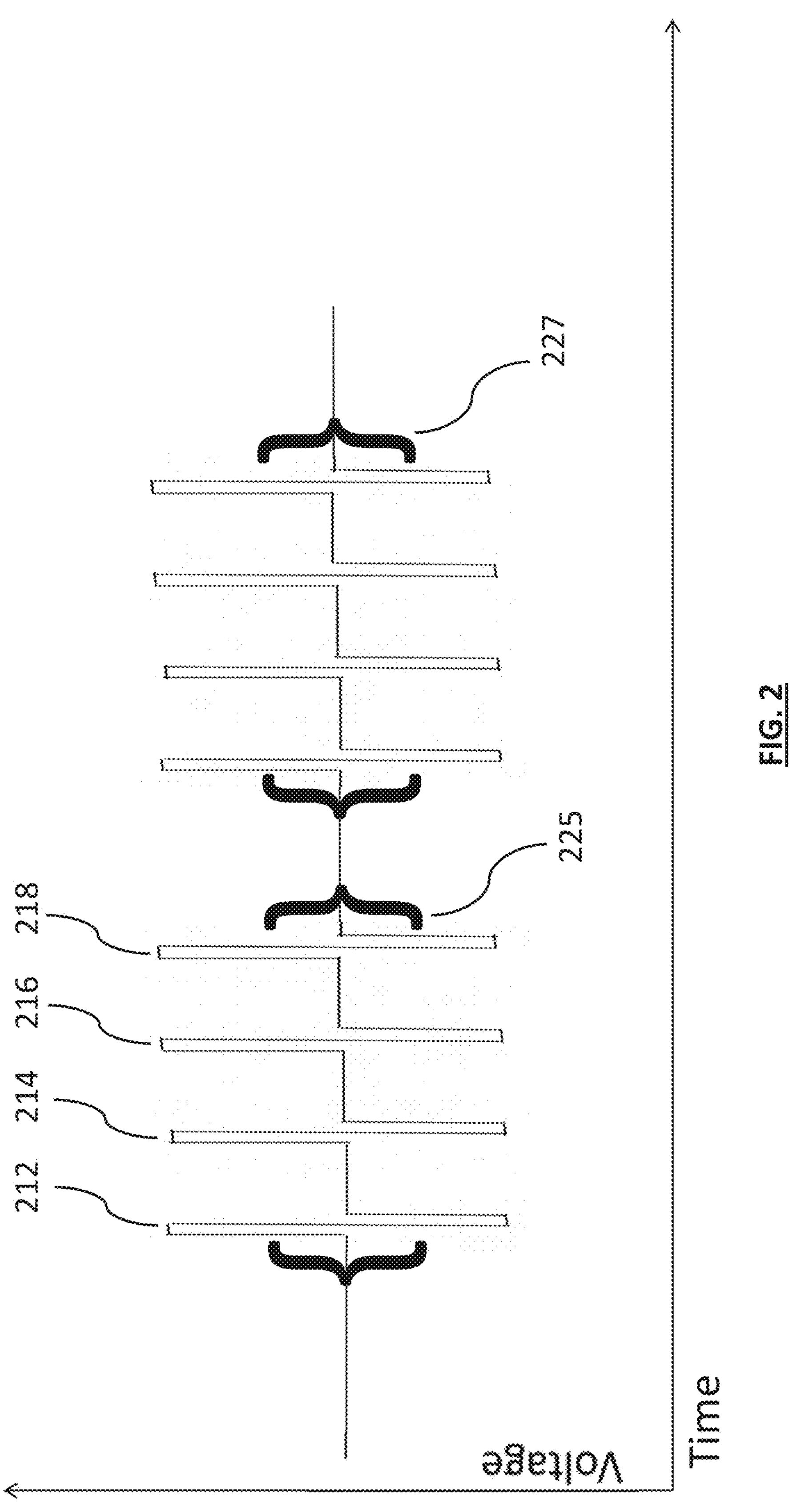
FIG. 2 illustrates multiple sets of voltage pre-ablation pulses, each set comprising pulses each applied to a distinct paired set of electrodes, according to embodiments.

FIG. 2 is a schematic illustration of multiple sets of voltage pre-ablation pulses each comprising multiple pulses each applied to a distinct pair or grouping of electrode subsets of an ablation device (e.g., ablation device 1310, 1310'). A first set of pulses 225 comprises four biphasic pulses 212, 214, 216, and 218 each applied to a different pair of electrode subsets. For example, the first set of pulses 225 may be followed by a second set of pulses 227 that comprise pulses each applied to a distinct pair of electrode subsets, and followed by additional sets of pulses. In some embodiments, each pair of electrode subsets receiving an individual pre-ablation pulse is an electrode subset pair that can also receive a pulse waveform during ablation delivery. Alternatively, different electrode subsets can receive the pre-ablation pulses and the ablation pulse waveform. For example, a first set of subsets of electrodes can receive the pre-ablation pulses, and a second set of subsets of electrodes can receive an ablation pulse waveform for delivery of ablation therapy. A current delivered during each pre-ablation pulse may be measured as described in more detail with respect to later figures presented herein. Multiple measurements can be obtained for each paired electrode subset by repeating the set of pulses, and can be used for averaging, noise reduction, and the like.

While FIG. 2 depicts four distinct pulses in each set of pulses, it should be apparent to one skilled in the art that any number of pulses can be utilized and correspond to the number of distinct pairs of electrode subsets needed for the measurement. For example, the number of pulses can correspond to the number of paired electrode subsets receiving ablation energy. In some embodiments, any number of sets of pulses or repeats can be implemented as convenient for measurement purposes. In some embodiments, the number of sets of pulses can be in the range of about 1 set to about 15 sets, with each set comprising at least one pulse applied to one pair of electrode subsets. Likewise, while FIG. 2 illustrates biphasic pre-ablation pulses 212, 214, 216, 218, the pre-ablation pulses may comprise monophasic pulses.

Figure 3:
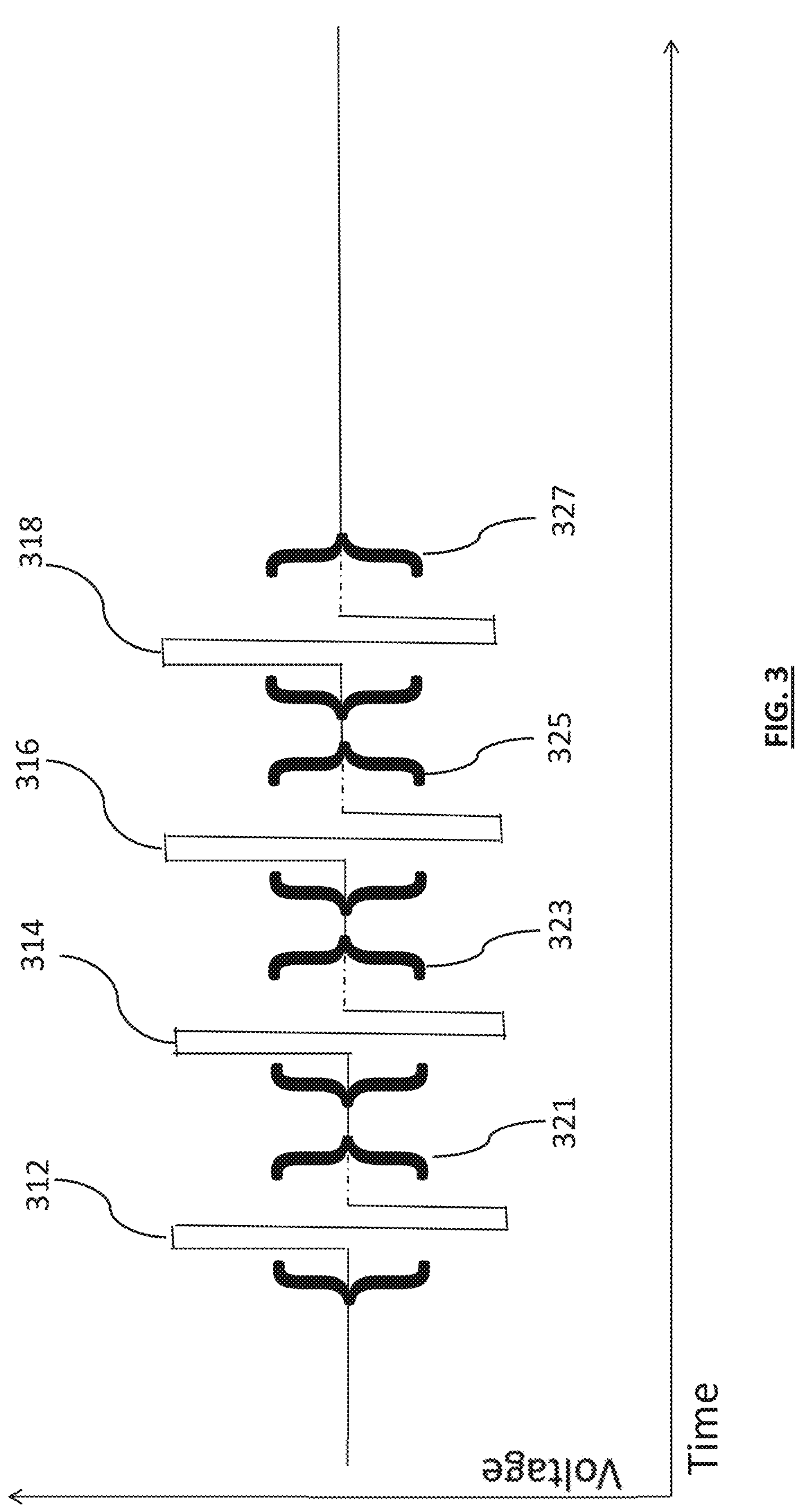
FIG. 3 shows multiple sets of multiple voltage pre-ablation pulses, each set applied to a distinct paired set of electrodes, according to embodiments.

FIG. 3 is a schematic illustration of multiple sets of multiple voltage pre-ablation pulses, with each set applied to a distinct paired set of electrodes (e.g. subset of electrodes) of an ablation device (e.g., ablation device 1310, 1310'). FIG. 3 depicts four sets of pulses 321, 323, 325, and 327. A first set of pulses 321 may comprise multiple biphasic pulses 312 each applied to a first pair of electrode subsets. A second set of pulses 323 may comprise multiple biphasic pulses 314 each applied to a second pair of electrode subsets. A third set pulses 325 may comprise multiple biphasic pulses 316 each applied to a third pair of electrode subsets. A fourth set of pulses 327 may comprise multiple biphasic pulses 318 each applied to a fourth pair of electrode subsets. The current delivered during each pre-ablation pulse may be measured as described in more detail herein. By repeating pulses applied to a particular pair of electrode subsets in each set of pulses, multiple measurements can be obtained for each paired electrode subset and may be used for averaging, noise reduction, and the like.

While FIG. 3 depicts four sets of pulses, it can be appreciated that any number of sets of pulses can be utilized depending on the number of distinct pairs of electrode subsets needed for the measurement. For example, in some embodiments the number of sets of pulses can correspond to the number of paired electrode subsets receiving ablation energy. In some embodiments, any number of sets of pulses or repeats can be implemented as convenient for measurement purposes. In some embodiments, the number of sets of pulses can be in the range of about 1 set to about 15 sets, with each pulse in a given set applied to the same pair of electrode subsets. Likewise, while FIG. 3 illustrates biphasic pre-ablation pulses 312, 314, 316, 318, the pre-ablation pulses may comprise monophasic pulses. In some embodiments, the pulse width of the pre-ablation pulses can be the same as the pulse width of pulses used in ablation energy delivery. In some embodiments, the pulse width of the pre-ablation pulses can be smaller than the pulse width of pulses used in ablation energy delivery. In some embodiments, the pulse width of the pre-ablation pulses can be larger than the pulse width of pulses used in ablation energy delivery. In some embodiments, the pulse width of the pre-ablation pulses illustrated in FIGS. 1A-3 can range from about nanoseconds to about hundreds of microseconds.

Figure 4A:
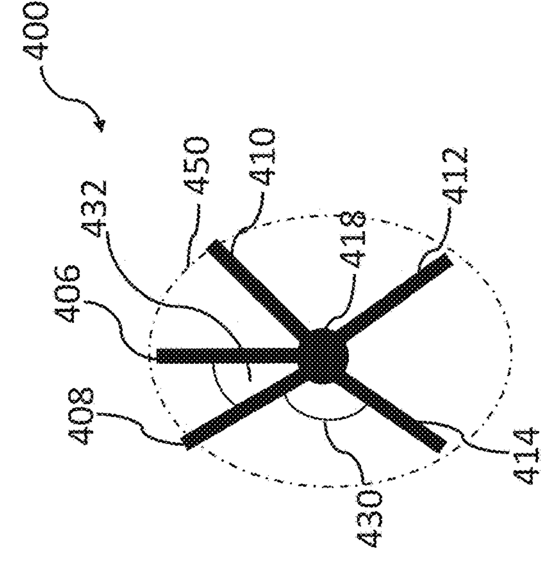
FIG. 4A schematically illustrates a deployable multi-spline catheter in a basket configuration, where the distal portion of the catheter comprises multiple splines that can be deployed over a range of configurations, according to embodiments.
Figure 4A:
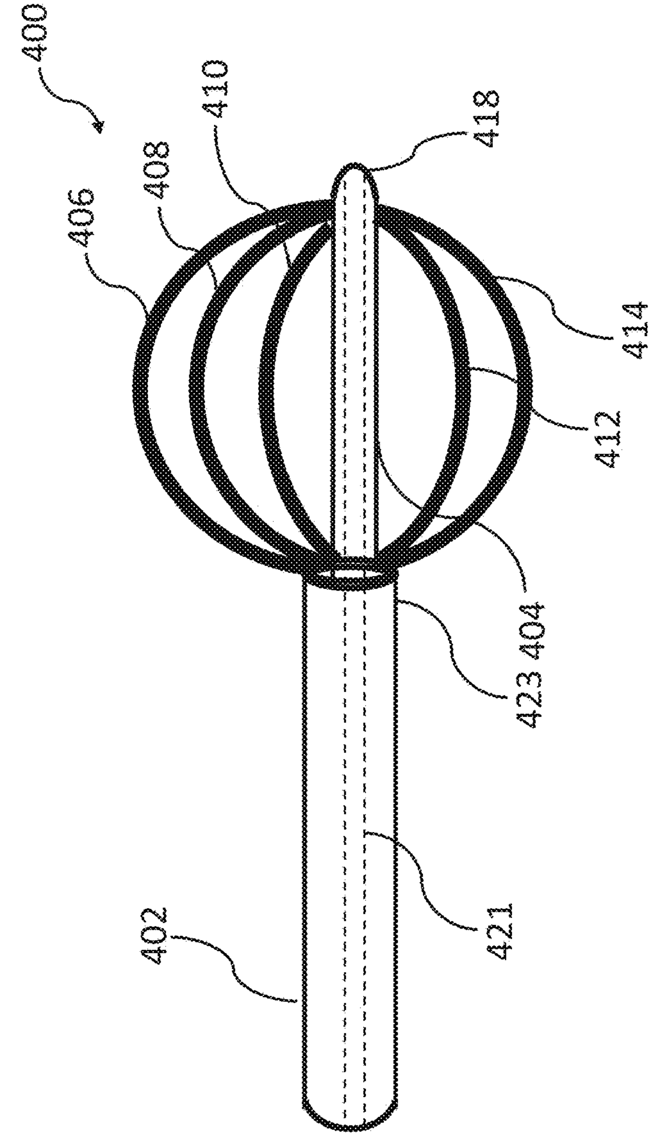

FIG. 4A schematically illustrates an ablation device (e.g., ablation device 1310, 1310') implemented as a deployable multi-spline catheter 400. The multi-spline catheter 400 can be deployed in a basket configuration, where a distal portion of the catheter 400 comprises a plurality of splines that may be deployed over a range of configurations. In some embodiments, each spline can have one or more electrodes configured for energy delivery, with each electrode disposed along a length of the spline. In some embodiments, the devices, systems, and methods disclosed herein may comprise one or more of the devices, systems, and methods described in International Application Serial No. PCT/US2018/29938, incorporated above by reference. The basket catheter 400 may comprise a first shaft 402 (e.g., outer shaft) comprising a distal end 423. A second shaft 404 (e.g., inner shaft) may extend through the first shaft 402 and the second shaft 404 may comprise a distal cap 418. The second shaft 404 may be configured to be deployed from a proximal catheter handle (not shown). In some embodiments, a guidewire lumen 421 may be configured to extend through the length of the second shaft 404 so that the catheter device 400 may be delivered over a guidewire to an anatomical region of interest.

In some embodiments, each of the distal splines 406, 408, 410, 412 and 414 has one or more electrodes (not shown) disposed along its length; for example, the number of electrodes can range from 1 to 20 depending on implementation. Each spline is attached at its distal end to distal cap 418 and at its proximal end to the distal end 423 of the outer shaft. When the inner shaft 404 is fully extended, the splines are in an undeployed configuration with the splines running mostly parallel to the inner shaft with only a slight convexity in the middle. As the inner shaft 404 is pulled in by manipulating a control at the catheter handle, the ends of the spline are brought closer together and the splines bow or curve outward, thereby deploying the basket. In some embodiments, the distal cap at the end of the inner shaft can be pulled back almost to the location of the distal end 423 of the outer shaft, in which case the splines of the basket fold or curve into petals and the fully deployed basket assumes the shape of a flower, as described in International Application Serial No. PCT/US2018/29938 and incorporated above by reference. The partially or fully deployed splines can be used to engage a portion of a patient anatomy, such as the pulmonary vein ostium of the cardiac left atrium. Once suitably engaged, pulsed field ablation can be delivered. For optimal therapy delivery, the splines of a partially deployed basket configuration of the splines or a fully deployed flower configuration would be fairly uniformly distributed about the long axis of the inner shaft 404. Significant non-uniformities in spatial distribution of the splines could on some occasions result in sub-optimal therapy delivery and/or excessive currents.

FIG. 4B is a schematic illustration of a front view of a deployed basket configuration of the deployable multi-spline catheter 400 where the distal portion of the catheter 400 comprises multiple splines that can be deployed over a range of configurations and where the splines are in a non-uniform arrangement due to anatomical constraints. FIG. 4B shows the spline basket viewed from the distal end where the distal cap 418 is visible along with splines 406, 408, 410, 412 and 414. Each of the distal splines 406, 408, 410, 412 and 414 may comprise one or more electrodes (not shown) disposed along its length for energy delivery. For example, the number of electrodes can range from about 1 electrode to about 20 electrodes. As shown in FIG. 4B, splines 406 and 408 form a first angle 432, and splines 408 and 414 form a second angle 430. Second angle 430 is larger than first angle 432, demonstrating significant non-uniformity of spline distribution. This type of non-uniform spline arrangement can be a consequence of local anatomic constraints such as non-circular pulmonary vein anatomy 450 or steep take-off angles of pulmonary veins with respect to the left atrium. In this example, when ablation is attempted with a non-uniform spline distribution and the non-uniformity of spline distribution is sufficient to cause one or more pre-ablation current analysis checks to fail, the pulsed field ablation system can output (e.g., display of input/output device 1327) a message to the user on a user interface prompting re-positioning of the device without delivering the ablation waveform. The user can then disengage from the target anatomy and re-deploy the device, re-engage the target anatomy, confirm uniformity of spline distribution on one or more fluoroscopic views, and then attempt ablation energy delivery once again. Upon delivery of a set of pre-ablation pulses, if the pre-ablation current analysis passes, then ablation waveforms may be delivered.

Figure 5:
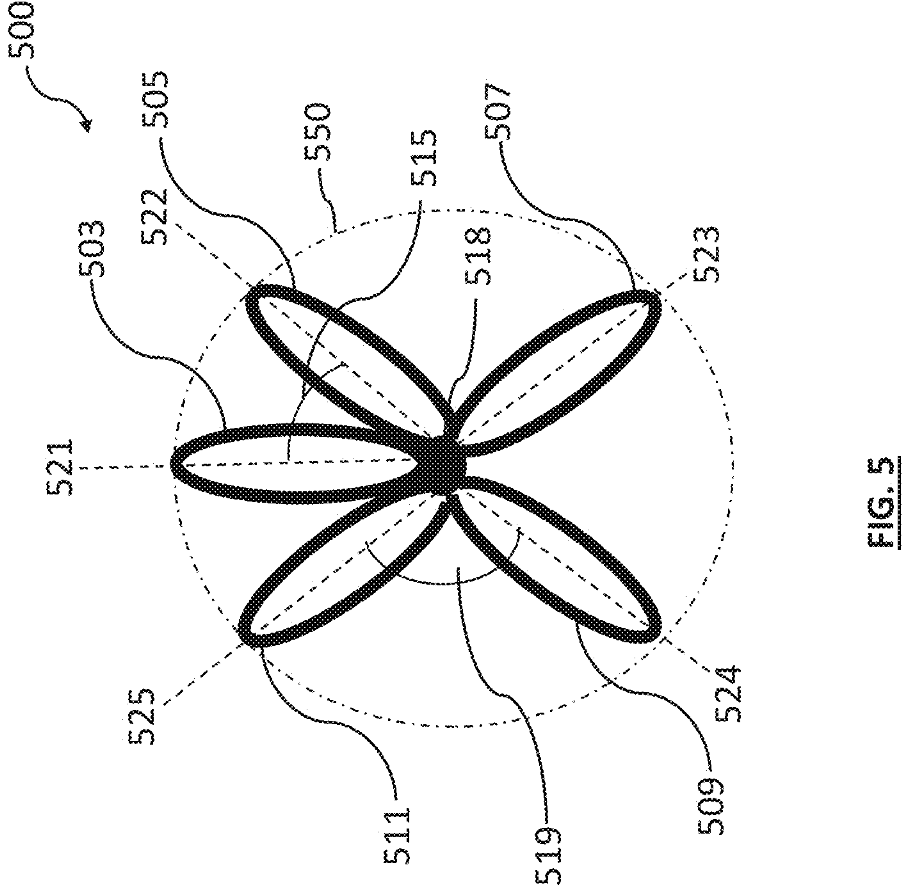
FIG. 5 is a schematic illustration of a front view of a deployed flower configuration of a deployable multi-spline catheter where the distal portion of the catheter comprises multiple splines that can be deployed over a range of configurations and where the splines or petals of the flower are in a non-uniform arrangement due to anatomical constraints, according to embodiments.

FIG. 5 is a schematic illustration of a front view (e.g., view from a distal end) of a fully deployed flower configuration of a deployable multi-spline catheter 500 (e.g., an ablation device 1310, 1310') where a distal portion of the catheter 500 comprises multiple splines that can be deployed over a range of configurations and where the splines (which may be formed like a petal of a flower) may be in a non-uniform arrangement due to anatomical constraints such as pulmonary veins 550 with eccentric cross sections. In FIG. 5, splines 503, 505, 507, 509 and 511 are deployed such that each spline assumes the form of a petal of a flower. In some embodiments, each of the distal splines 503, 505, 507, 509 and 511 may comprise one or more electrodes (not shown) disposed along its length for energy delivery. In some embodiments, the number of electrodes on each spline can range from about 1 electrode to about 20 electrodes. Apical lines 521, 522, 523, 524 and 525 may be drawn from the distal cap 518 to the apex (e.g., point on each spline farthest away from the distal cap 518) of respective splines 503, 505, 507, 509 and 511. A first angle 515 made by splines 503 and 505 may be measured as the angle between respective apical lines 521 and 522. A second angle 519 made by splines 509 and 511 may be measured as the angle between respective apical lines 524 and 525. Second angle 519 may be significantly larger than first angle 515, thereby representing a non-uniform petal distribution due to the pulmonary veins 550.

The non-uniform spline (e.g., petal) distributions illustrated respectively in FIGS. 4B and 5 may result in sub-optimal therapy delivery and/or excessive currents. In such situations, the distribution of measured pre-ablation currents with pre-ablation pulses can provide information that can drive a decision to proceed with ablation or to re-position the device before delivering ablation, as described in more detail herein. While FIGS. 4A, 4B, and 5 illustrate baskets with five splines, these embodiments are non-limiting and is provided for exemplary purposes only. It should be apparent that basket embodiments with other numbers of splines, for example from about 3 splines to about 16 splines, can be implemented as convenient for the application. In some embodiments, one or more of the spline electrodes can also be used to record electrogram data corresponding to electrical activity of the heart.

Figure 6A:
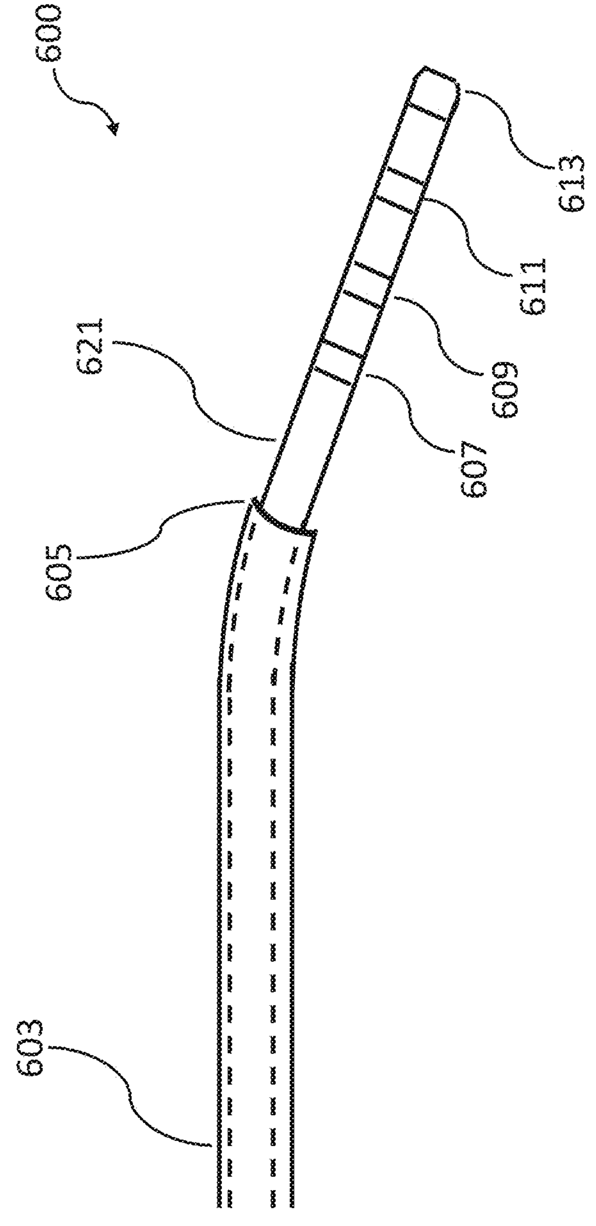
FIG. 6A schematically illustrates a linear focal catheter with multiple electrodes disposed along its distal portion extending from a sheath with all the electrodes exposed beyond the distal end of the sheath, according to embodiments.

FIG. 6A schematically illustrates a linear focal catheter 600 (e.g., ablation device 1310, 1310') with multiple electrodes disposed along its distal portion extending from a sheath with all the electrodes exposed beyond the distal end of the sheath. For example, a catheter 621 may be configured to translate through a sheath or delivery device 603 which may have a curve, either fixed or steered, to navigate the focal catheter 600 to a region of interest such as a target anatomical location. The catheter 621 may comprise a distal portion that extends beyond the distal end 605 of the sheath 603 and comprise a plurality of electrodes 607, 609, 611, and a distal tip electrode 613 disposed at a distal end of the catheter 621. In FIG. 6A, all the distal electrodes 607, 609, 611, 613 of the catheter 621 are exposed outside the sheath 603. While four distal electrodes are shown in the example illustrated in FIG. 6A, a different number of electrodes may be implemented. For example, other embodiments can have from about 2 electrodes to about 20 electrodes that are engaged for pulsed field ablation energy delivery.

In some pulsed field ablation applications, it may be desirable to engage at least a minimum number of electrodes for bipolar ablation energy delivery where paired electrode subsets are used to deliver ablation energy. For example, a bipolar ablation delivery scheme may be used for pulsed field ablation using a linear focal catheter. For example, the devices, systems, and methods disclosed herein may comprise one or more of the devices, systems, and methods described in International Application Serial No. PCT/US2020/37948, incorporated above by reference. Delivering energy to a minimum number of electrodes for pulsed field ablation energy delivery can facilitate therapy delivery and avoid excessively large local current densities and associated thermal effects. For example, in some cardiac applications, at least a minimum number of electrodes may be extended beyond the sheath 603 into a blood pool and the distal catheter tip electrode 613 may be positioned at an ablation site for local ablation energy delivery at that site for lesion generation. In some embodiments, the catheter 600 may comprise a location sensor (e.g., electromagnetic) configured to track a catheter tip location within a cardiac chamber. In some embodiments, the catheter tip location may be displayed on an anatomical map or electro-anatomical map of the cardiac chamber.

Figure 6B:
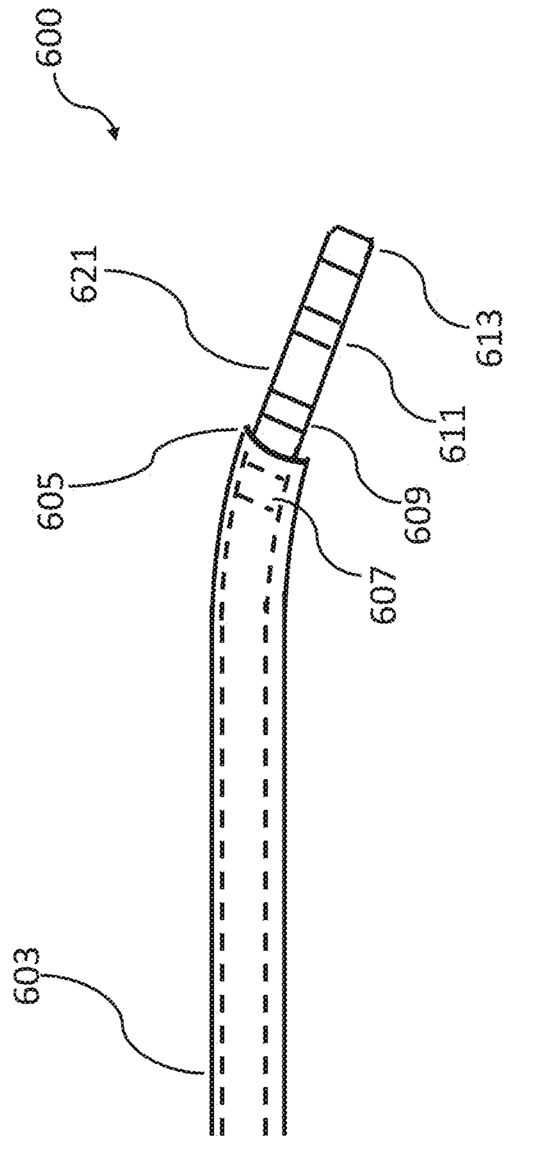
FIG. 6B schematically illustrates a linear focal catheter with multiple electrodes disposed along its distal portion extending from a sheath with some of the electrodes, but not all of them exposed beyond the distal end of the sheath, according to embodiments.

FIG. 6B schematically illustrates the linear focal catheter 600 with multiple electrodes disposed along its distal portion and with some, but not all, of the electrodes extending from a sheath 603. For example, the catheter 621 passes through a sheath or delivery device 603 which may have a curve, either fixed or steered, to navigate the focal catheter 600 to a region of interest such as a target anatomical location. The portion of the catheter 621 that extends beyond the distal end 605 of the sheath 603 may comprise three electrodes 609, 611, and distal tip electrode 613 disposed along its length, while electrode 607 is inside the sheath 603 and not exposed. In this example, four electrodes would be engaged for optimal pulsed field ablation energy delivery. In some embodiments, the configuration illustrated in FIG. 6A may be sub-optimal and result in inadequate lesion generation from pulsed field ablation energy delivery since electrode 607 is not exposed. In such situations, measured pre-ablation currents with pre-ablation pulses can provide information that can drive a decision to proceed with ablation or to re-position the device before delivering ablation energy. For example, the number of exposed electrodes may be determined by measuring a current of a pre-ablation pulse, and a user can be prompted to re-position and/or re-deploy the device to ensure exposure of a predetermined number of electrodes. When an insufficient number of electrodes are exposed, the measured current of a set of pre-ablation pulses may prompt device redeployment. In some embodiments, a pulsed field ablation system can display a message to the user on a user interface requesting repositioning of the device while inhibiting ablation waveform delivery. The user can disengage from the target anatomy using visualization (e.g., under an imaging modality such as fluoroscopy) and re-engage the target anatomy to redeploy the device and ensure exposure of the ablation electrodes. An ablation waveform may be delivered based upon a subsequent set of pre-ablation signal current measurements passing predetermined checks.

While FIGS. 6A and 6B illustrate a linear catheter with four electrodes, the number of electrodes illustrated is non-limiting and is provided for exemplary purposes only. It should be apparent that embodiments with other numbers of electrodes, for example from about two electrodes to about twenty electrodes, can be implemented as convenient.

Figure 7:
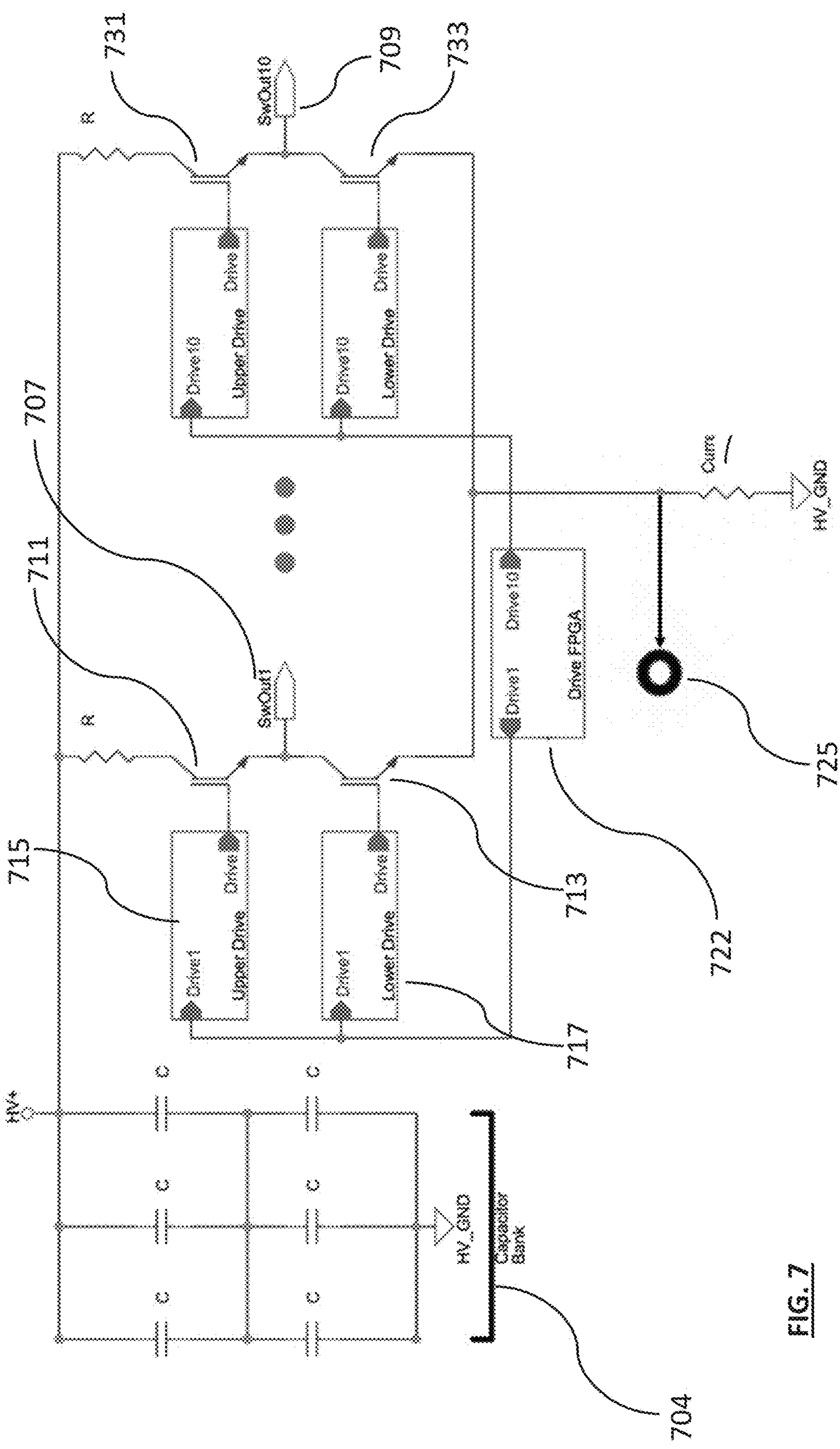
FIG. 7 illustrates a circuit topology for generation of high voltage pulses for application to a set of electrodes and measurement of associated currents, according to embodiments.

FIG. 7 illustrates a circuit diagram for generating high voltage pulses to a set of electrodes for pulsed field ablation and measurement of associated currents, according to embodiments. The circuit diagram depicted in FIG. 7 can be coupled to or be part of a signal generator, such as, for example, signal generator 1320. In some embodiments, the devices, systems, and methods disclosed herein may comprise one or more of the devices, systems, and methods described in International Application Serial No. PCT/US2018/19552, incorporated above by reference. FIG. 7 illustrates an energy source implemented as a capacitor bank 704 configured to charge to a predetermined source voltage using a charging power supply circuit (not shown) and configured to store energy for release to electrodes for pre-ablation pulse delivery and/or pulsed field ablation energy delivery. In some variations, the capacitor 704 can be charged to a voltage of between about 500 V and about 10,000 V or more in order to generate a lesion with pulsed field ablation. In some variations, an ablation waveform may be generated by a series of upper half bridge switches 711 and 731 (e.g., transistors) and lower half bridge switches 713 and 733 (e.g., transistors), where corresponding upper and lower transistors can be paired to form a full bridge circuit depending on a desired pairing of electrodes for bipolar energy delivery. The outputs 707, 709 are coupled to corresponding electrodes (not shown). Each upper transistor 711 and lower transistor 713 may have a corresponding upper drive circuit 715 and lower drive circuit 717 for opening and closing the switches to provide a predetermined pulsed waveform output. A processor (e.g., any one of processor(s) 1324 as described with reference to FIGS. 13A and 13B) implemented as a drive FPGA 722 is configured to execute instructions to open and close switches (e.g., switches 711, 713, 731, 733) with appropriate timing in order to output predetermined pulsed waveforms to the electrodes, e.g., for either the delivery of pre-ablation pulse waveforms or for the delivery of ablation waveforms (which are generally different from the pre-ablation pulse waveform). The return path to capacitor ground or lower terminal may pass through components of sensing circuitry, including, for example, a current sense resistor 720 and corresponding pulsed current measurement circuitry 725. Generally, the capacitor bank 704 may be charged based on a voltage input provided by a user on a pulsed field ablation system user interface (e.g., part of Input/Output Device 1327) for ablation energy delivery. In some embodiments, the capacitor voltage can be larger than the ablation voltage input provided by a user on a user interface, e.g., to account for resistive losses. In some embodiments, the voltage amplitude used for ablation energy delivery may also be the voltage amplitude used for pre-ablation pulses.

Figure 8:
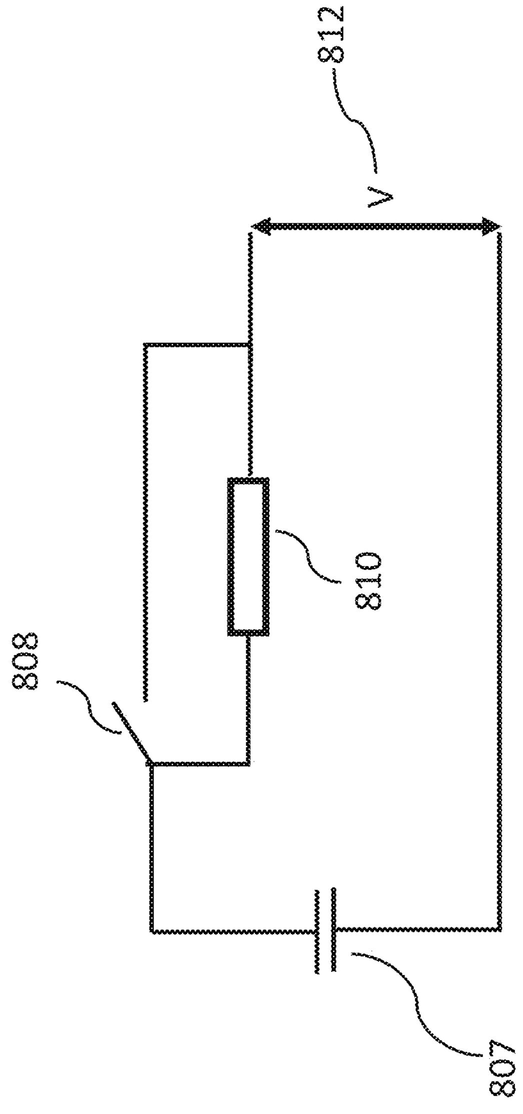
FIG. 8 illustrates a schematic circuit topology for generation of pre-ablation pulses, according to embodiments.
Figure 8:

In some embodiments, a voltage amplitude of a pre-ablation pulse can be smaller than the voltage amplitude of an ablation pulse. FIG. 8 illustrates a schematic circuit diagram for generating pre-ablation pulses, according to embodiments. The circuit may comprise an energy source implemented as a capacitor 807 such as a capacitor bank (e.g., capacitor bank (704)) connected to a switch 808 and resistor 810 network. The switch 808 can switch between open and closed states. The switch 808 is open when reduced-voltage pre-ablation pulses are output. For example, the resistor 810 is connected to capacitor 807 and generates a voltage drop so that the source voltage 812 (e.g., voltage provided to pulsing switches 711, 713) is smaller than the capacitor voltage of capacitor 807. When ablation pulses are output (e.g., once the measured pre-ablation pulse current checks pass predetermined criteria), the switch 808 may close so that the current path is directly through the switch and does not pass through resistor 810 such that the source voltage 812 is the same as the capacitor voltage of capacitor 807. In some embodiments, the switch 808 can be one or more of a solid-state switch (e.g., IGBT, MOSFET) or a relay. In some embodiments, the resistor 810 can have a resistance that can vary, e.g., be set based on input provided by a user.

Figure 9:
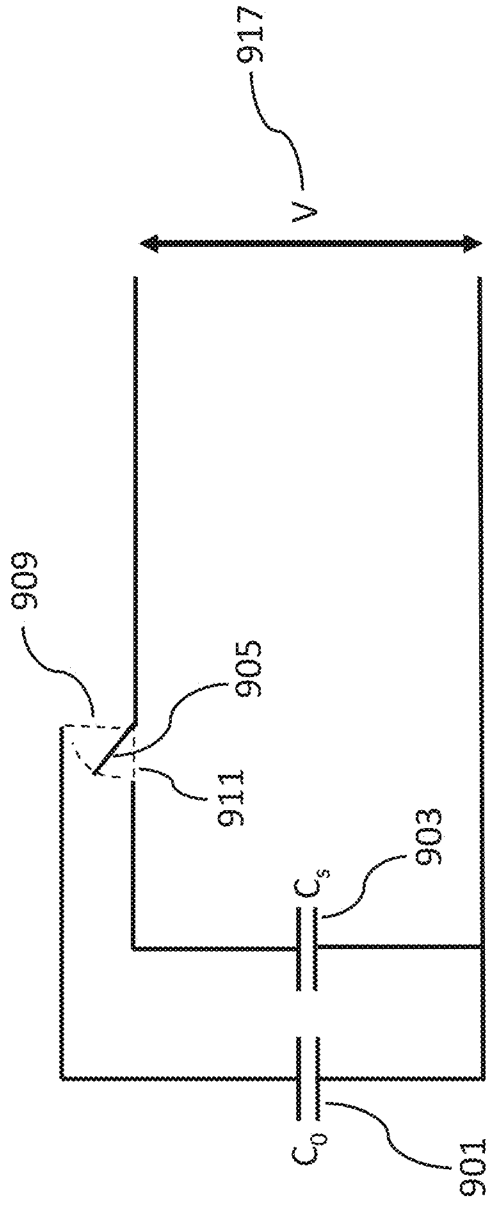
FIG. 9 illustrates another schematic circuit topology for generation of pre-ablation pulses that uses a second capacitor charged to a lower voltage than a first capacitor, according to embodiments.
Figure 9:

FIG. 9 illustrates another schematic circuit diagram for generating pre-ablation pulses using a second capacitor charged to a lower voltage than a first capacitor, according to embodiments. The circuit may comprise a first energy source implemented as a first capacitor 901 such as a capacitor bank (e.g., capacitor bank (704)) connected to a second energy source implemented as a second capacitor 903 and switch network 905. The second capacitor 903 may be charged to a voltage less than the voltage of the first capacitor 901 and can be used for lower voltage pre-ablation pulses. The switch 905 can be configured to switch between first and second positions. In some embodiments, switch 905 may be set to closed position 911 (e.g., a first position) closing the circuit with second capacitor 903 when pre-ablation pulses are desired, and the lower voltage of second capacitor 903 corresponds to the source voltage 917 (e.g., provided to the pulsing switches 711, 713) for delivery of pre-ablation signals or pulses. When ablation pulses are output (e.g., once the measured pre-ablation pulse current checks pass predetermined criteria), switch 905 may be set to open position 909 (e.g., a second position), thereby closing the circuit with first capacitor 901 such that the voltage of the first capacitor 901 corresponds to the source voltage 917 (e.g., provided to the pulsing switches 711, 713) for delivery of ablation pulses. In some embodiments, the switch 905 can be one or more of a solid-state switch (e.g., IGBT, MOSFET) and relay.

Figure 10:
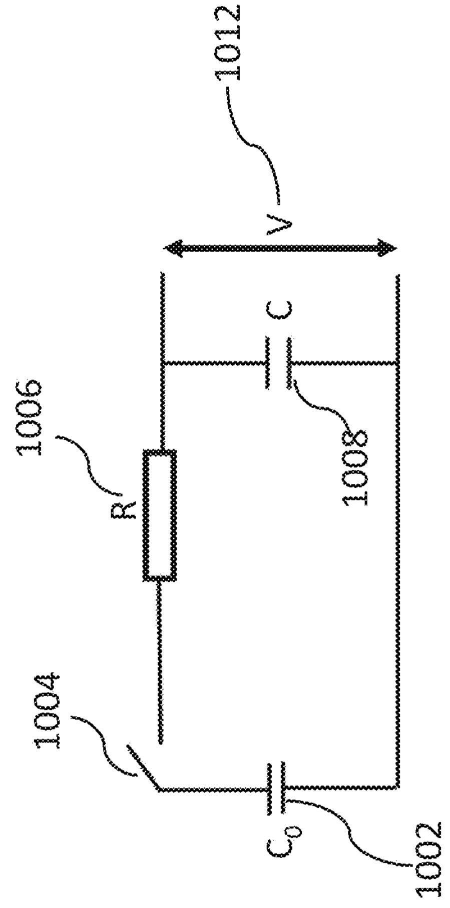
FIG. 10 depicts another schematic circuit topology for generation of pre-ablation pulses that utilizes fast switching and a resistor-capacitor network, according to embodiments.
Figure 10:

FIG. 10 depicts another schematic circuit diagram for generating pre-ablation pulses using fast switching and a second capacitor, according to embodiments. The circuit may comprise an energy source implemented as a first capacitor 1002 such as a capacitor bank (e.g., capacitor bank (704)) connected to a resistor-capacitor network such as switch 1004 with resistor 1006 and second capacitor 1008. The switch 1004 may comprise a solid-state device such as a MOSFET device that can be rapidly toggled between open and closed configurations when pre-ablation pulses are output. The resistor 1006 may have a resistance on the order of about 10 ohms or less to limit the voltage drop across resistor 1006. Furthermore, the resistor 1006 and second capacitor 1008 values may be selected such that a time constant (RC) is shorter than the pulse widths used for either pre-ablation pulses or ablation pulses.

For example, when pre-ablation pulses are output, the switch 1004 may be rapidly toggled between ON and OFF states (e.g., switched between closed and open states) at a frequency f such that $$2\pi f > \frac{1}{RC},$$

where R is the value of the resistance of the resistor 1006 and C is the value of the capacitance of the capacitor 10008. The RC circuit may then behave like a voltage divider where the net voltage across second capacitor 1008 is smaller than the voltage of first capacitor 1002. In some embodiments, the voltage across second capacitor 1008 corresponds to the source voltage 1012 (e.g., provided to the pulsing switches 711, 713) for pre-ablation pulses. When ablation pulses are output (e.g., once the measured pre-ablation pulse current checks pass predetermined criteria), switch 1004 may be kept closed and the voltage of first capacitor 1002 may correspond to the approximate source voltage (given the constraints that the resistor value R is small and that the time constant RC is much shorter than the pulse widths used for ablation pulses) provided to the pulsing switches 711, 713 for delivery of ablation pulses.

Figure 11:
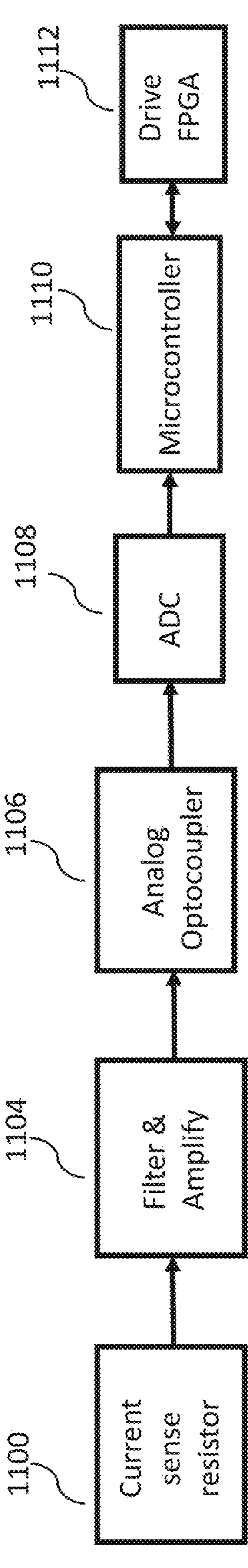
FIG. 11 is a block diagram of an apparatus for fast measurement of currents associated with voltage pulses, according to embodiments.

FIG. 11 provides a block diagram for measurement of currents corresponding to voltage pulses (e.g., delivery of pre-ablation signals), according to embodiments. The current through a current sense resistor (e.g., current sense resistor 720) may be sensed (e.g., in the form of a voltage drop) by measurement circuitry, at 1100. The signal may be filtered and amplified, e.g., by suitable filters, amplifiers, or other electronic components, at 1104. An analog optocoupler isolates any high-voltage noise in the signal from low-voltage circuits, at 1106. A high-speed analog-to-digital converter (ADC) digitizes the signal to produce a digital output, at 1108.

The digitized values or digital output may be received by a microcontroller (e.g., a processor, such as, for example, processor(s) 1324, as described with reference to FIGS. 13A and 13B) and buffered for analysis, at 1110. One or more samples of the measured current (in the form of digitized values or digital output) can be analyzed in the microcontroller to refine the current measurement. For example, if multiple pre-ablation pulses are delivered to a given pair of electrode subsets, the corresponding multiple current measurements can be filtered or refined according to several methods known in the art, for example such as averaging, discarding outliers and then averaging, weighted averaging, and the like. The measured currents from pre-ablation pulses delivered to several pairs of electrode subsets can be analyzed by the microcontroller to determine whether such currents meet one or more predetermined criteria. For example, the measured currents can be analyzed to determine if they are within a predetermined range of minimum and maximum values. In some embodiments, the criteria may include determining that no measured current exceeds a predetermined threshold value (e.g., maximum value), or determining that no measured current is smaller than a predetermined threshold value (e.g., minimum value). In some embodiments, the criteria may include computing a metric, such as, for example, the average value of the measured currents. In some embodiments, the metric may include one or more of computing the variance of the measured currents, computing the ratio of maximum to minimum measured currents, or generally computing an output of a non-linear function of the measured currents. In some embodiments, the criteria may include any combination of the computations described herein and further determining whether the computed quantities are within a predetermined range. For example, a predetermined criterion may include determining whether the variance of the measured currents is within a predetermined range. As another example, a predetermined criterion may include determining whether the ratio of the maximum current to minimum current lies below a threshold value. In some embodiments, the predetermined range or threshold values can be user-adjustable.

In some embodiments, the microcontroller is coupled with the drive FPGA (e.g., FPGA 722) that drives pulse and waveform generation, at 1112. If any of the predetermined criteria of the measured pre-ablation currents is not met, the microcontroller may send a signal to the FPGA to inhibit ablation energy delivery and/or alert the user (e.g., by generating an alert). For example, the microcontroller can output a message or alert on a graphical user interface (e.g., part of Input/Output Device 1327) requesting the user to re-position or re-deploy the device before ablation energy delivery. If the predetermined criteria of the pre-ablation pulses are met, the FPGA may be instructed to deliver ablation energy. Once ablation energy delivery is complete, the FPGA can send a message to the microcontroller indicating successful completion of ablation energy delivery. In this manner, pre-ablation pulse delivery followed by ablation delivery can be made seamless. By appropriately selecting criteria of the measured currents and corresponding threshold values, ablation energy can be delivered seamlessly when device deployment is appropriate.

Figure 12:
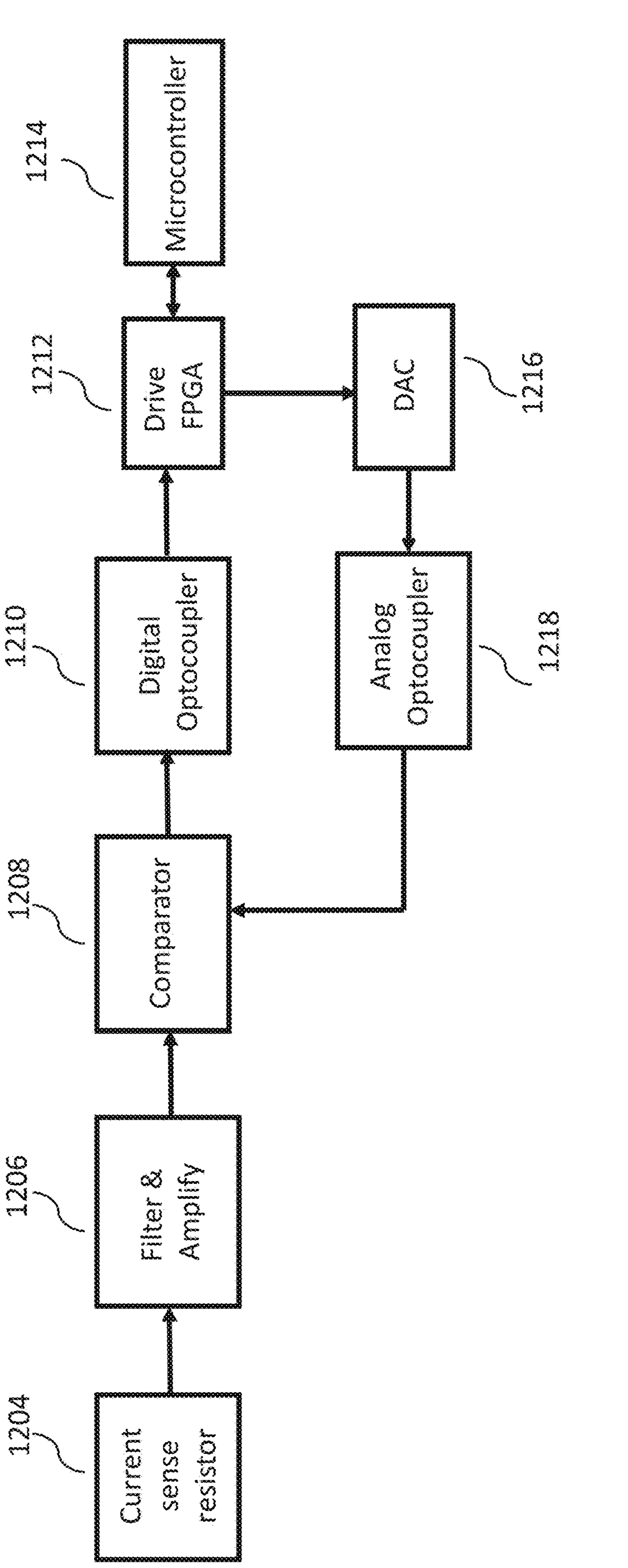
FIG. 12 is a block diagram of an alternate apparatus for ultra-fast measurement of currents associated with voltage pulses, according to embodiments.

FIG. 12 illustrates a block diagram of a current measurement device configured for ultra-fast measurement of currents associated with voltage pulses, according to embodiments. Such measurements may be useful, for example, when the pre-ablation pulses are very short pulses (less than a few microseconds) and analog-to-digital converters with sufficient read-out speeds or an adequate number of channels are not be available. Certain components described with respect to FIG. 12 can be structurally and/or functionally similar as those described with respect to FIG. 11. Therefore, certain descriptions with respect to FIG. 12 may be shortened given that such descriptions were provided with respect to FIG. 11. In FIG. 12, the pre-ablation pulse current that passes through a current sense resistor (e.g., current sense resistor 720) is sensed (in the form of a voltage drop) by measurement circuitry, at 1204. The signal is filtered and amplified, e.g., via appropriate filters, amplifiers, and/or other electronic circuitry, at 1206. The signal is received at a comparator (e.g., differential amplifier) where the analog signal is checked, for example to ensure that the current measurement meets a predetermined criterion, e.g., is within a predetermined range or window or is above or below predetermined thresholds, at 1208. The result of this comparison is passed through a digital optocoupler configured to isolate low-voltage circuits from high-voltage noise, at 1210. The signal is then received at a drive FPGA (e.g., drive FPGA 722 in FIG. 7), at 1212. If the current meets the predetermined criterion, e.g., is within a predetermined range or is above or below a predetermined threshold, at 1208, the FPGA may inform a microcontroller (e.g., a processor, such as, for example, processor(s) 1324, as described with reference to FIGS. 13A and 13B) and proceeds to deliver an ablation waveform, at 1214. If the current is not within a predetermined range, or fails predetermined threshold checks at 1208, the FPGA may inform the microcontroller and inhibit ablation energy delivery. For example, the microcontroller can output a message or alert on a graphical user interface (e.g., part of Input/Output Device 1327) requesting the user to reposition or redeploy the device before delivering ablation energy.

In some embodiments, the predetermined range (or window) of current values can be user-adjustable. Upon ablation request by the user, the microcontroller may send an input range of current values or current thresholds to the drive FPGA, and thereafter to a digital-to-analog converter (DAC) for conversion to an analog signal, at 1216. The analog range of current values or current thresholds may be passed through an analog optocoupler, at 1218, to ensure isolation of low-voltage circuits (such as the digital-to-analog converter) from any high voltage noise, and then passed to the comparator. The analog signal may be used to set a window range or threshold values in the comparator, at 1208. In embodiments where a predetermined range or window of current values, or threshold values may not be not user-adjustable, predetermined or default values may be stored in the microcontroller and the window range in the window comparator may be set in the same manner as described herein.

The apparatus and methods disclosed here can verify device deployment or positioning prior to ablation energy delivery. While specific device embodiments are described herein for exemplary purposes, it should be apparent that other device embodiments can also be implemented as convenient as determined by one skilled in the art and without limitation.

Figure 14:
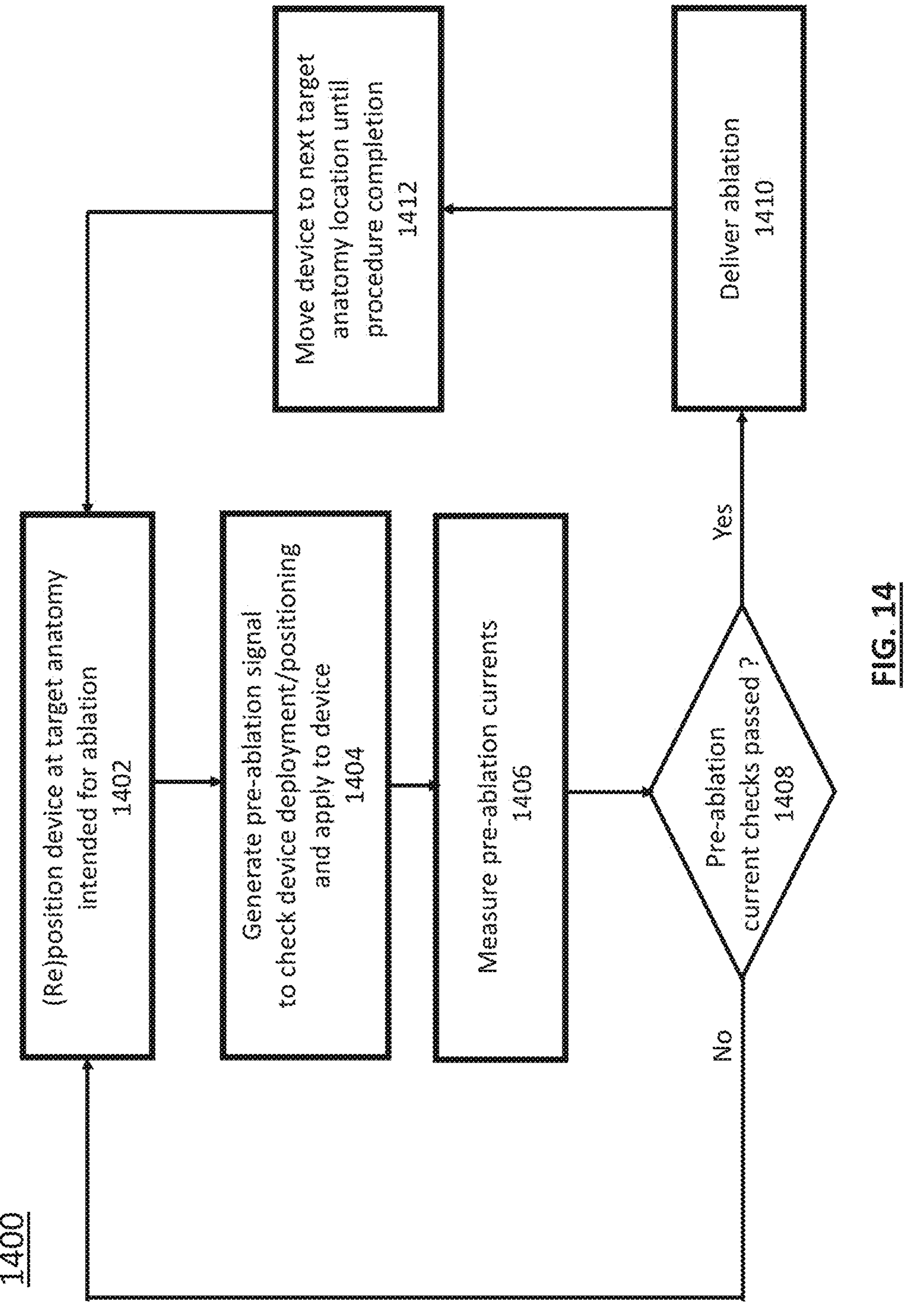
FIG. 14 illustrates a method for tissue ablation, according to embodiments.

FIG. 14 is an example method 1400 of tissue ablation. In some embodiments, a current of a pre-ablation signal as described herein may be measured and used to determine whether a device delivers ablation energy or is repositioned prior to ablation delivery. The method 1400 includes positioning a device (e.g., device 400, 500, 600, 1310, 1310') at a target anatomy for ablation energy delivery (e.g., into an endocardial space such as a left or right atrium or left or right ventricle), at 1402. A pre-ablation signal may be generated and applied to the device to confirm proper device positioning/deployment at 1404. For example, a set of pre-ablation signals may be generated by a signal generator (e.g., signal generator 1320). Each pre-ablation signal can be delivered to a subset of electrode channels or electrodes, e.g., according to a predetermined sequence. The pre-ablation currents (e.g., currents passing through a sensing resistor or measurement circuitry as described herein) may be measured for each pre-ablation signal that is delivered to a subset of electrode channels or electrodes, at 1406. A determination of whether the device positioning/deployment passes a predetermined set of checks or criteria based on measured pre-ablation currents may be performed, at 1408. For example, as described herein, the measured pre-ablation currents can be analyzed to check that each lies within a predetermined range of minimum and maximum values. In embodiments, the check can comprise determining that no pre-ablation current exceeds a predetermined maximum value. In some embodiments, the check can comprise determining that no pre-ablation current is below a predetermined minimum value. In embodiments, the check can comprise computing a metric such as the average value of the pre-ablation currents. In embodiments the check can comprise computing a metric such as the variance of the pre-ablation currents, computing a metric such as the ratio of maximum to minimum pre-ablation currents, or computing a metric based on some other generally non-linear function of the pre-ablation currents. In embodiments, the check can comprise any combination of these computations (e.g., computing a metric or a plurality of metrics based on one or more of these computations), and then determining whether the computed metric(s) lie inside a predetermined range or whether they fall below or exceed appropriate predetermined threshold values. For example, in one embodiment the check can be to determine whether the variance of the measured currents lies within a certain range. As another example, in one embodiment, the check can be to determine whether the ratio of the maximum current to minimum current lies below a threshold value. In some embodiments, this threshold value can be greater than about 1 and less than about 5, greater than about 1 and less than about 10, greater than about 1 and less than about 20, including all sub-values and ranges in-between. If the measured currents do not meet one or more predetermined criteria, the user may be prompted (e.g., alerted) to reposition the device, at 1402. If the device is properly positioned, then ablation energy may be delivered to the device, e.g., in the form of an ablation pulse waveform, at 1410. The device may be moved to a next target anatomy location and the procedure continued in this manner until ablation therapy is completed, at 1412.

The ablation pulse waveforms may include a plurality of levels of a hierarchy to optimize pulsed field ablation energy delivery, e.g., as described in International Application Serial No. PCT/US2019/031135, filed on May 7, 2019, titled "SYSTEMS, APPARATUSES AND METHODS FOR DELIVERY OF ABLATIVE ENERGY TO TISSUE," the contents of which are hereby incorporated by reference in its entirety. In some embodiments, the tissue ablation thus performed may be delivered in the absence of ectopic cardiac activity and in synchrony with paced heartbeats or with native cardiac ECG activity to reduce the risk of atrial and/or ventricular fibrillation and damage to healthy tissue. It should be appreciated that any of the ablation devices described herein (e.g., device 400, 500, 600, 1310, 1310'), or a variety of other ablation devices with at least one electrode for delivery of pulsed field ablation energy, may be used to ablate tissue using the methods discussed herein as appropriate.

In some embodiments, the ablation devices described herein (e.g., device 400, 500, 600, 1310, 1310') may be used for epicardial and/or endocardial ablation. Examples of suitable ablation catheters are described in International Application Serial No. PCT/US2019/014226, incorporated above by reference.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2019/014226, incorporated above by reference.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). It should be appreciated that the steps described in certain figures may be combined and modified as appropriate.

It should be understood that the examples and illustrations in this disclosure serve exemplary purposes and departures and variations such as numbers of splines, number of electrodes, and so on can be built and deployed according to the teachings herein without departing from the scope of this invention. While specific parameters such as sampling frequency, time intervals and so on were given for exemplary purposes only in the description herein, it should be understood that other values of the various parameters can be used as convenient for the application by those skilled in the art based on the teachings presented in this disclosure.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention.

The invention claimed is:

1. A system, comprising:

an ablation device including a set of electrodes configured to be positioned within patient anatomy;

a signal generator including:

an energy source coupled to the set of electrodes; and sensing circuitry coupled to the set of electrodes; and a processor operatively coupled to the energy source and the sensing circuitry, the processor configured to:

generate, using the energy source, a set of pre-ablation signals;

deliver the set of pre-ablation signals to a first set of subsets of electrodes of the set of electrodes;

measure, using the sensing circuitry, a set of one or more currents passing through a current sense resistor of the sensing circuitry in response to the delivery of the set of pre-ablation signals;

determine whether the set of currents meet a predetermined criterion by determining whether the set of currents is at least one of: (i) greater than a predetermined threshold value, (ii) less than a predetermined threshold value, or (iii) within a predetermined range of values; and in response to determining that the set of currents meet the predetermined criterion, generate and deliver a pulse waveform to a second set of subsets of electrodes of the set of electrodes such that the second set of subsets of electrodes generates a pulsed electric field for ablating tissue;

wherein each pre-ablation signal from the set of pre-ablation pulses includes at least one pulse each having a first amplitude, and the pulse waveform includes at least one pulse each having a second amplitude, the first amplitude being less than the second amplitude;

wherein the signal generator further includes:

a resistor; and a switch configured to switch between open and closed states;

the switch in the open state configured to couple the resistor to the energy source such that the resistor generates a voltage drop that reduces a voltage of the energy source to produce the at least one pulse having the first amplitude; and the switch in the closed state configured to decouple the resistor from the energy source to produce the at least one pulse having the second amplitude.

2. The system of claim 1, wherein the processor is further configured to:

in response to determining that the set of currents do not meet the predetermined criterion, generate an alert instructing a user to reposition the ablation device.

3. The system of claim 1, wherein the processor is configured to determine whether the set of currents meet the predetermined criterion by:

calculating a metric based on at least one of: an average value of the set of currents, a variance of the set of currents, or a ratio of a maximum current to a minimum current of the set of currents; and determining whether the metric is less than or greater than a threshold value.

4. The system of claim 1, wherein the signal generator further includes a set of electrode channels, each electrode channel of the set of electrode channels including a first switch from a first plurality of switches and a second switch of a second plurality of switches, the energy source being coupled to a collector terminal of the first switch of each electrode channel of the set of electrode channels, and the current sense resistor being coupled to an emitter terminal of the second switch of each electrode channel of the set of electrode channels.

5. The system of claim 1, wherein each pre-ablation signal of the set of pre-ablation signals includes a single biphasic pulse.

6. The system of claim 1, wherein each pre-ablation signal of the set of pre-ablation signals includes a plurality of biphasic pulses.

7. The system of claim 1, wherein the first set of subsets of electrodes is the same as the second set of subsets of electrodes.

8. The system of claim 1, wherein the processor is configured to deliver the set of pre-ablation pulses to the first set of subsets of electrodes according to a predetermined sequence in which each pre-ablation pulse from the set of pre-ablation pulses is delivered to a distinct subset of electrodes of the first set of subsets of electrodes.

9. The system of claim 1, wherein each pre-ablation signal from the set of pre-ablation pulses includes at least one pulse each having a first width, and the pulse waveform includes at least one pulse each having a second width, the first width being different from the second width.

10. The system of claim 1, wherein the energy source is a first energy source, and the signal generator further includes:

a second energy source having a voltage that is greater than a voltage of the first energy source; and the switch in the first state configured to close a circuit with the first energy source to produce the at least one pulse having the first amplitude, and the switch in the second state configured to close a circuit with the second energy source to produce the at least one pulse having the second amplitude.

11. The system of claim 1, wherein the ablation device includes a set of splines and the set of electrodes is distributed on the set of splines, the set of splines configured to transition from an undeployed configuration to a deployed configuration in which the set of splines curve outward from a longitudinal axis of the ablation device, the set of splines in the deployed configuration configured to be positioned within a heart of a patient, the processor further configured to determine that a subset of splines of the set of splines are non-uniformly distributed in response to determining that the set of currents do not meet the predetermined criterion.

12. The system of claim 1, wherein the ablation device includes a single linear shaft slidably positioned within a sheath, the linear shaft having a distal portion that supports the set of electrodes, the linear shaft extendable distal to the sheath to expose one or more electrodes of the set of electrodes for ablation, the processor further configured to determine that a minimum number of electrodes required for ablation has not been exposed from the sheath in response to determining that the set of currents do not meet the predetermined criterion.

13. The system of claim 1, wherein the sensing circuitry is configured to measure signals indicative of current passing through the current sense resistor, the signal generator further including:

an analog optocoupler coupled to the sensing circuitry, the analog optocoupler configured to isolate high-voltage noise from the signals measured by the sensing circuitry; and an analog-to-digital converter (ADC) configured to digitize the signals after the analog optocoupler has isolated the high-voltage noise from the signals and to pass the signals to the processor, the processor configured to determine whether the set of currents meets the predetermined criterion after receiving the signals from the ADC.

14. An apparatus, comprising:

a current sense resistor coupled to a set of electrodes of an ablation device positionable within patient anatomy;

current measurement circuitry configured to measure a current across the current sense resistor that is generated in response to a pre-ablation pulse being applied to a first subset of electrodes of the set of electrodes;

a comparator configured to determine whether the current meets a predetermined criterion and to produce a digital output indicative of whether the current meets the predetermined criterion; and a processor configured to:

in response to the digital output indicating that the current meets the predetermined criterion, cause delivery of a pulse waveform to a second subset of electrodes of the set of electrodes such that the second subset of electrodes generates a pulsed electric field for ablation; and in response to the digital output indicating that the current does not meet the predetermined criterion, inhibit delivery of the pulse waveform to the second subset of electrodes;

wherein the processor is configured to set the predetermined criterion based on an input received from a user;

wherein the input includes a threshold value or a range of values, and the processor is configured to set the predetermined criterion by:

passing the threshold value or the range of values to a digital-to-analog converter (DAC) such that the DAC produces an analog signal representative of the threshold value or the range of values, the predetermined criterion being set at the comparator based on the analog signal.

15. The apparatus of claim 14, wherein the processor includes a field programmable gate array (FPGA) configured to execute instructions to open and close a set of switches to cause the delivery of the pulse waveform to the second subset of electrodes.

16. The apparatus of claim 14, wherein the processor is further configured to, in response to the digital output indicating that the current does not meet the predetermined criterion, generate an alert instructing an user to reposition the ablation device.

17. The apparatus of claim 14, further comprising a digital optocoupler coupled to the comparator, the digital optocoupler configured to isolate high-voltage noise from the digital output.

18. The apparatus of claim 14, wherein the comparator is configured to determine whether the current meets the predetermined criterion by at least one of: determining whether the current is greater than a predetermined threshold value, determining whether the current is less than a predetermined threshold value, or determining whether the current is within a predetermined range of values.

19. The apparatus of claim 18, further comprising an analog optocoupler configured to isolate high-voltage noise from the analog signal before the analog signal is passed to the comparator.

20. A method, comprising:

generating, using an energy source, a set of pre-ablation signals;

delivering the set of pre-ablation signals to a first set of subsets of electrodes of the set of electrodes of an ablation device, the ablation device being position within patient anatomy;

measuring, using sensing circuitry coupled to the set of electrodes, a set of one or more currents passing through a current sense resistor of the sensing circuitry in response to the delivery of the set of pre-ablation signals;

determining whether the set of currents meet a predetermined criterion; and in response to determining that the set of currents meet the predetermined criterion, generating and delivering a pulse waveform to a second set of subsets of electrodes of the set of electrodes such that the second set of subsets of electrodes generates a pulsed electric field for ablating tissue;

wherein determining whether the set of currents meets the predetermined criterion includes at least one of: determining whether each current of the set of currents is greater than a predetermined threshold value, determining whether each current of the set of currents is less than a predetermined threshold value, or determining whether each current of the set of currents is within a predetermined range of values;

wherein the set of pre-ablation signals is delivered to the first set of subsets of electrodes according to a predetermined sequence in which each pre-ablation signal from the set of pre-ablation signals is delivered to a distinct subset of electrodes of the first set of subsets of electrodes.

21. The method of claim 20, further comprising:

in response to determining that the set of currents do not meet the predetermined criterion, generating an alert instructing a user to reposition the ablation device.

22. The method of claim 21, wherein determining whether the set of currents meets the predetermined criterion includes:

calculating a metric based on at least one of: an average value of the set of currents, a variance of the set of currents, or a ratio of a maximum current to a minimum current of the set of currents; and determining whether the metric is less than or greater than a threshold value.

* * * * *